United States Patent
Kohm et al.

(10) Patent No.: US 8,372,115 B2
(45) Date of Patent: Feb. 12, 2013

(54) BONE SUPPORT DEVICE, SYSTEM AND METHOD

(75) Inventors: Andrew Kohm, San Mateo, CA (US); Janna Clark, Belmont, CA (US); Samuel Lee, San Francisco, CA (US); Thomas A. Slater, Sunnyvale, CA (US)

(73) Assignee: Kyphon SARL, Neuchatel (CH)

( * ) Notice: Subject to any disclaimer, the term of this patent is extended or adjusted under 35 U.S.C. 154(b) by 0 days.

(21) Appl. No.: 13/231,738

(22) Filed: Sep. 13, 2011

(65) Prior Publication Data
US 2012/0004728 A1   Jan. 5, 2012

Related U.S. Application Data

(63) Continuation of application No. 11/713,771, filed on Mar. 2, 2007.

(51) Int. Cl.
*A61B 2/44* (2006.01)

(52) U.S. Cl. ...... 606/246; 606/105; 606/914; 623/17.11

(58) Field of Classification Search ............ 606/57, 606/63, 86 A, 86 R, 90, 92–95, 99, 102, 105, 606/282; 623/17.11–17.16
See application file for complete search history.

(56) References Cited

U.S. PATENT DOCUMENTS

| | | | | |
|---|---|---|---|---|
| 6,960,215 B2 * | 11/2005 | Olson et al. | ..................... | 606/92 |
| 7,465,318 B2 * | 12/2008 | Sennett et al. | ............. | 623/17.12 |
| 7,799,078 B2 * | 9/2010 | Embry et al. | ............. | 623/17.11 |
| 2002/0123750 A1 * | 9/2002 | Eisermann et al. | ............. | 606/69 |
| 2005/0261781 A1 * | 11/2005 | Sennett et al. | ............. | 623/23.54 |
| 2006/0100706 A1 * | 5/2006 | Shadduck et al. | ......... | 623/17.11 |
| 2007/0088436 A1 * | 4/2007 | Parsons et al. | ............. | 623/17.11 |
| 2007/0173939 A1 * | 7/2007 | Kim et al. | .................. | 623/17.11 |
| 2008/0071356 A1 * | 3/2008 | Greenhalgh et al. | ......... | 623/1.16 |
| 2009/0204216 A1 * | 8/2009 | Biedermann et al. | ...... | 623/17.12 |

* cited by examiner

*Primary Examiner* — Eduardo C Robert
*Assistant Examiner* — Jerry Cumberledge
(74) *Attorney, Agent, or Firm* — Sorell, Lenna and Schmidt LLP

(57) ABSTRACT

A bone support and/or barrier device and having an implantable structure including an outer surface, an inner surface, a first bone contact portion, and a second bone contact portion. The structure is collapsible to an undeployed configuration capable of percutaneous insertion to the interior of a bone and expandable to a deployed configuration in the bone. In the deployed configuration, the first bone contact portion contacts a first portion of the bone, and the second bone contact portion contacts a second portion of the bone such that a load placed on the first portion of the bone is transferred through the implantable structure to the second portion of the bone. The implantable structure includes a barrier material adapted to restrict bone filler material inserted into the bone adjacent the inner surface of the structure from flowing to the outer surface of the structure. A method is also disclosed.

8 Claims, 13 Drawing Sheets

BONE SUPPORT DEVICE, SYSTEM AND METHOD

CROSS REFERENCE TO RELATED APPLICATIONS

This application is a continuation of co-pending U.S. patent application Ser. No. 11/713,771 filed Mar. 2, 2007, which is incorporated herein by reference in its entirety.

FIELD OF THE INVENTION

The present invention relates to bone support and/or barrier devices and systems, kits comprising a bone support and/or barrier device, and related methods. Embodiments of the present invention can be advantageous for providing support and/or barrier to a bone accessed by a minimally invasive technique or other surgical technique.

BACKGROUND OF THE INVENTION

Bone may become fractured or prone to compression fracture or collapse due to various conditions, including osteoporosis, avascular necrosis, cancer, trauma, or other disease. If not successfully treated, fractured or weakened bone can result in deformities, chronic complications, and an overall adverse impact upon the quality of life.

Minimally invasive surgical procedures have been developed that can be used to treat fractured bones. Such minimally invasive procedures can reduce pain, post-operative recovery time, and the destruction of healthy tissue. In minimally invasive surgery, the site of pathology is accessed through portals rather than through a significant incision, thus preserving the integrity of intervening tissues. These minimally invasive techniques also often require only local anesthesia.

Minimally invasive surgical techniques are particularly desirable for spinal and neurosurgical applications because of the need for access to locations deep within the body and the danger of damage to vital intervening tissues associated with conventional "open" access techniques. The development of minimally invasive spinal procedures, for example, for repair of vertebral compression fractures, has resulted in reduced recovery time and decreased post-operative pain as such procedures require minimal, if any, muscle dissection and can be performed under local anesthesia.

Minimally invasive procedures for reducing a vertebral compression fracture ("VCF") can include inserting a bone tamp, such as an expandable balloon, curette, and/or other device into a vertebral body. The bone tamp can be used to create a void, or interior cavity, in the cancellous bone in the vertebral body. The void can be filled with a filling material, such as a bone cement, in order to provide interior structural support for cortical bone.

In certain applications, it may be desirable to provide structural support to a bone structure after a void has been created inside the bone structure. For example, a bone tamp may be utilized to create a void inside a vertebral body and displace an endplate of the vertebral body to restore the height of the vertebral body. In certain clinical situations, it may be desirable to provide structural support to the endplate in order to maintain the position of the endplate after the bone tamp has been removed prior to injection of bone cement to fill the void.

In certain disease states, such as osteoporosis, vertebral bodies may be particularly susceptible to VCF. Moreover, patients who have suffered a VCF may be at risk for additional VCFs. The occurrence or reoccurrence of VCFs may be related to collapse of an endplate into the vertebral body.

Thus, in certain medical situations, it may be desirable to provide structural support to the endplate of a vertebral body to prevent the endplate from collapsing. In clinical situations in which the height of a collapsed vertebral body has been restored, it may be desirable to provide structural support to maintain the height of the endplate.

SUMMARY OF THE INVENTION

Embodiments of the present invention can provide bone support and/or barrier devices and systems, kits comprising a bone support and/or barrier device, and related methods. Some embodiments are useful for supporting a bony structure in an interior body region in a human or animal accessed utilizing minimally invasive surgery.

In an illustrative embodiment, the bone support device can comprise an implantable structure having an outer surface, an inner surface, a first bone contact portion, and a second bone contact portion. A portion of the outer surface can comprise the first bone contact portion. The structure can be collapsible to an undeployed configuration capable of percutaneous insertion to the interior of a bone and expandable to a deployed configuration in the interior of the bone. In some embodiments, when the structure is in the deployed configuration, the first bone contact portion can contact at least a first portion of the bone from the interior of the bone, and the second bone contact portion can contact at least a second portion of the bone. In this manner, a load placed on the first portion of the bone can be transferred through the implantable structure to the second portion of the bone. In certain embodiments, the device can be implanted in a vertebral body such that the first bone contact portion of the device can contact an endplate and the second bone contact portion can contact cortical bone about a perimeter of the vertebral body, for example, the cortical bone in the vertebral body side wall.

In some embodiments, the bone support device can comprise a structure that when deployed can extend between the superior endplate and the inferior endplate in a vertebral body. In this manner, a load placed on the superior endplate can be transferred through the device to the inferior endplate to provide structural support to the superior endplate. In certain embodiments, the bone support device can comprise a structure that when deployed can contact the endplate and both the cortical bone in the vertebral body side wall and the cortical bone in the inferior endplate. Such a configuration can provide structural support to the superior endplate by transferring a load from the superior endplate to both the vertebral body side wall and the inferior endplate.

In some embodiments, the bone support device may be utilized to provide structural support to the interior of a bone without use of any additional support mechanisms, for example, injection of a bone cement. In other embodiments, the bone support device may be inserted into the interior of a bone, and a bone cement can be injected into the bone interior to provide further structural support to the bone.

In some embodiments, the implantable structure can include a barrier material attached to the structure that is adapted to prohibit substantially all of a bone filler material inserted into the bone adjacent the inner surface of the structure from flowing to the outer surface of the structure.

Other embodiments can comprise a system or a kit including an implantable bone support device having an outer surface, an inner surface, a first bone contact portion, and a second bone contact portion. The device can be releasably attached to the distal end of an elongate member, such as a deployment cannula, in an undeployed configuration. Such a system or kit can further include a delivery cannula having a hollow lumen that can be percutaneously inserted into the interior of a bone. The elongate member and the attached bone support device may be inserted through the lumen of the delivery cannula to the bone interior.

A system or kit can further include a deployment mechanism that can be inserted through the lumen of the delivery cannula and actuated to deploy the bone support device into a deployed configuration in the interior of the bone. In some embodiments, the system or kit can also include a release mechanism adapted to release the bone support device from the elongate member. Some embodiments of a system or kit can include a plurality of the implantable bone support devices, in which each of the devices can be inserted into the interior of a bone and deployed such that the deployed configurations support a separate portion of the bone.

Some embodiments of the present invention can comprise a barrier material that can be inserted into the interior of a bone and adapted to prohibit substantially all of a bone filler material inserted into the bone from flowing through and/or around the barrier material. Such embodiments of a barrier material may prevent the undesirable flow of the bone filler material into and through a compromised portion of the bone. For example, an embodiment of a such a barrier material inserted into a void created in the interior of a vertebral body may prevent the flow of subsequently injected bone cement through and/or around the barrier material into a compromised endplate and/or vertebral body wall. In this manner, the barrier material may prevent leakage of the bone cement through the endplate and/or vertebral body wall. Such embodiments of a barrier material may be utilized without any other structural supports.

Other embodiments can comprise a method for supporting a bone utilizing an implantable bone support device. The bone support device can comprise an outer surface, an inner surface, a first bone contact portion, and a second bone contact portion. The device can be releasably attached to the distal end of an elongate member in an undeployed configuration. The elongate member and attached bone support device can be percutaneously inserted into the interior of a bone. In some embodiments, such a method can further include actuating a deployment mechanism to deploy the bone support device into a deployed configuration. Deploying the device into a deployed configuration can cause the first bone contact portion to contact at least a first portion of the bone from the interior of the bone, and the second bone contact portion to contact at least a second portion of the bone. In this manner, a load placed on the first portion of the bone can be transferred through the device to the second portion of the bone. For example, in certain embodiments, the device can be implanted in a vertebral body such that the first bone contact portion of the device can contact an endplate and the second bone contact portion can contact cortical bone about a perimeter of the vertebral body, for example, the cortical bone in the vertebral body side wall. Some embodiments of a method may further include selectively positioning the bone support device in a desired location and orientation in the interior of the bone prior to, during, or after actuating the deployment mechanism. In certain embodiments, a method can include releasing the bone support device from the elongate member. The elongate member may then be removed from the bone. In some embodiments, such a method may further include inserting an expandable body into the interior of a bone, such as a vertebral body, and expanding the expandable body to create a void and/or move a collapsed or partially collapsed endplate so as to restore the height of the vertebral body.

Features of a bone support device, system, kit, and methods of the present invention may be accomplished singularly, or in combination, in one or more of the embodiments of the present invention. As will be realized by those of skill in the art, many different embodiments of a bone support device, system, kit, and method for supporting a bone according to the present invention are possible. Additional uses, advantages, and features of embodiments of the invention are set forth in the illustrative embodiments discussed in the detailed description herein and will become more apparent to those skilled in the art upon examination of the following.

BRIEF DESCRIPTION OF THE DRAWINGS

FIG. 14B shows a bone support device delivered on the distal end of an elongate member through the delivery cannula into the interior of the vertebral body. FIG. 14C shows the delivery cannula retracted toward the extra-pedicular entry site in the vertebral body wall and the bone support device being further deployed in the interior of the vertebral body.

DETAILED DESCRIPTION

Embodiments of the present invention can provide bone support and/or barrier devices, systems, and kits, and methods. Some embodiments are useful for supporting a bony structure in an interior body region in a human or animal accessed utilizing a minimally invasive surgery technique. The devices, systems, kits, and methods can be adapted for use in many suitable interior body regions, wherever the support, repair, and/or protection of one or more layers of tissue may be required for a therapeutic or diagnostic purpose. The illustrative embodiments are associated with devices, systems, kits, and methods used to treat bones. Other embodiments may be utilized in other interior body regions or with other types of tissues.

As used in this specification and the appended claims, "proximal" is defined as nearer to a point of reference such as an origin, a point of attachment, or the midline of the body. As used in this specification and the appended claims, "distal" is defined as farther from a point of reference, such as an origin, a point of attachment, or the midline of the body. Thus, the words "proximal" and "distal" refer to, for example, direction nearer to and farther from, respectively, an operator (for example, surgeon, physician, nurse, technician, etc.) who inserts a medical device into a patient, with the distal end, or tip, of the device inserted inside the patient's body. For example, the end of a medical device inserted inside the patient's body is the distal end of the medical device, while the end of the medical device outside the patient's body is the proximal end of the medical device.

Figure 1:
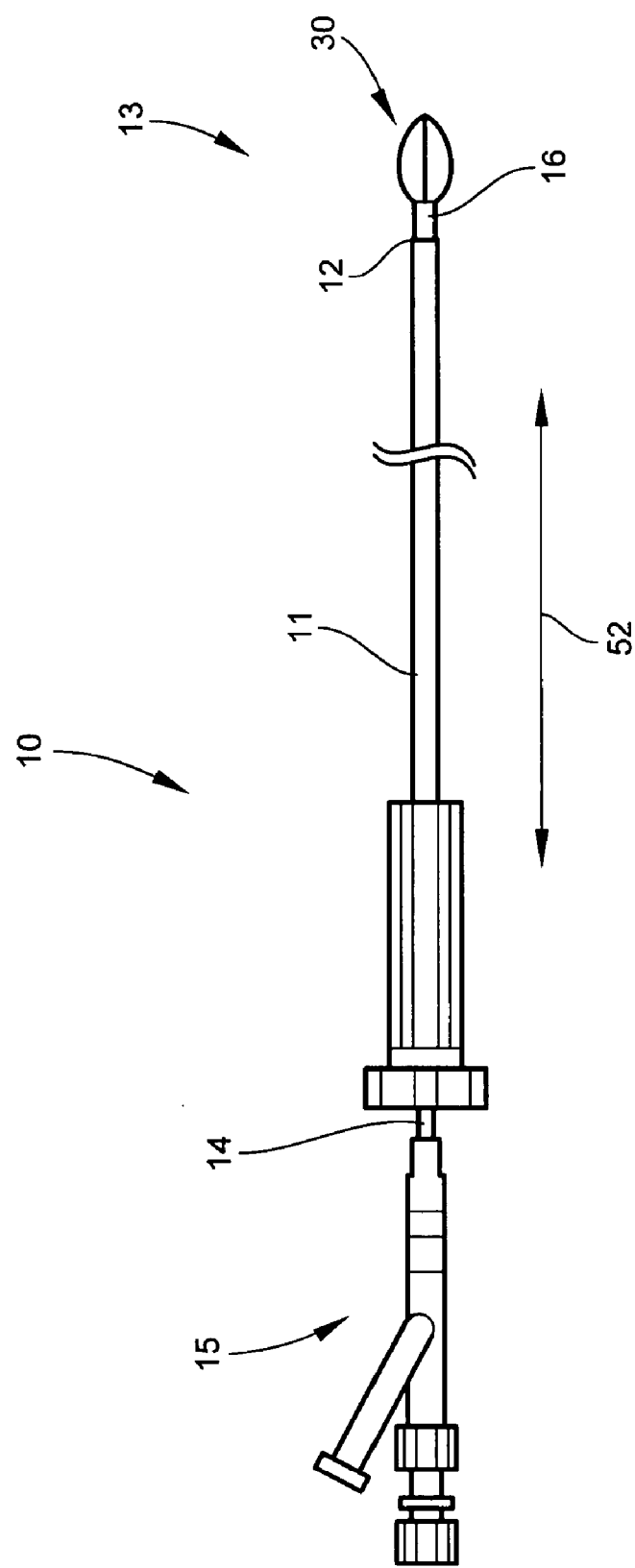
FIG. 1 is a side view of a bone support device system having an implantable structure attached to the distal end of an elongate member inserted through a delivery cannula in an embodiment of the present invention.

Referring now to the figures, FIG. 1 is a view of a system 10 according to an embodiment of the present invention comprising a bone support and/or barrier device 13. The system 10 is configured to allow an user to deliver and/or deploy the bone support and/or device 13 in a targeted area in an interior body region, such as the interior 33 of a bone. The system 10 includes an implantable structure 30 attached to the distal end 16 of the elongate member 14 that is configured to be used, for example, in a minimally invasive procedure for repairing a vertebral compression fracture.

As shown in FIG. 1, the system 10 can comprise a delivery cannula 11 having a proximal end and a distal end 12. The delivery cannula 11 may be fabricated from a material selected to facilitate advancement and rotation of the elongate member 14 movably disposed within a hollow lumen of the delivery cannula 11. The delivery cannula 11 can be constructed, for example, using standard flexible, medical grade plastic materials, such as vinyl, polyamides, polyolefins, ionomers, polyurethane, polyether ether ketone (PEEK), polycarbonates, polyimides, and polyethylene tetraphthalate (PET). The delivery cannula 11 can be constructed as a bi-layer or a tri-layer of one or more of these materials. The delivery cannula 11 can also comprise more rigid materials to impart greater stiffness and thereby aid in its manipulation and torque transmission capabilities. More rigid materials useful for this purpose include stainless steel, nickel-titanium alloys (such as Nitinol), and other metal alloys.

The embodiment of the system 10 shown in FIG. 1 comprises the elongate member 14 movably disposed within the delivery cannula 11. The elongate member 14 can be have a hollow lumen that allows for movement of a flowable material, for example, a liquid or a gas, through the elongate member 14. The elongate member 14 may be made from a resilient inert material providing torsion transmission capabilities, for example, stainless steel, a nickel-titanium alloy such as Nitinol, and other suitable metal alloys. In other embodiments, the elongate member 14 may be fashioned from a variety of suitable materials, such as a carbon fiber, a glass, or a flexible material, for example, as a plastic or rubber. In an embodiment comprising a flexible elongate member 14, the elongate member 14 may be formed, for example, from twisted wire filaments, such as stainless steel, nickel-titanium alloys (such as Nitinol), and other suitable metal alloys.

Figure 4:
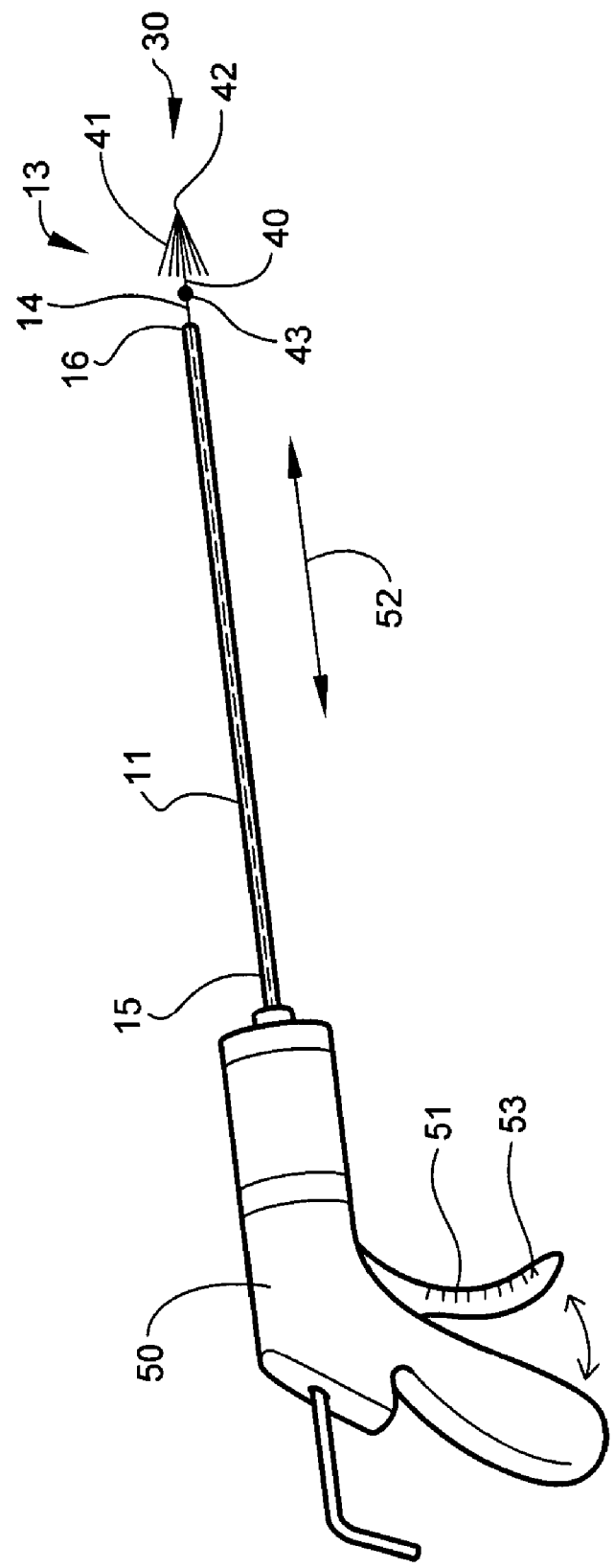
FIG. 4 is a side view of a bone support device attached to the distal end of an elongate member and a handle having a deployment mechanism attached to the proximal end of the elongate member in an embodiment of the present invention.

The elongate member 14 may include a handle 50, for example, as shown in FIG. 4, at its proximal end 15 to aid in gripping and maneuvering the elongate member 14. Such a handle 50 can be formed from a plastic or foam material and secured about the proximal end 15 of the elongate member 14. In some embodiments, the elongate member 14, and thereby the implantable structure 30, may be in communication with a controller, such as a slide controller, a pistol grip controller (as shown in FIG. 4), a ratcheting controller, a threaded controller, or any other suitable type of controller that can be configured to permit a user of the system 10 to control the extent to which the implantable structure of the bone support device extends beyond the distal end 16 of the elongate member 14. Such a controller may permit a user of the system 10 to manipulate the implantable structure 30, for example, to provide rotational torque and thereby control rotation of the elongate member 14 and the implantable structure 30.

Figure 2:
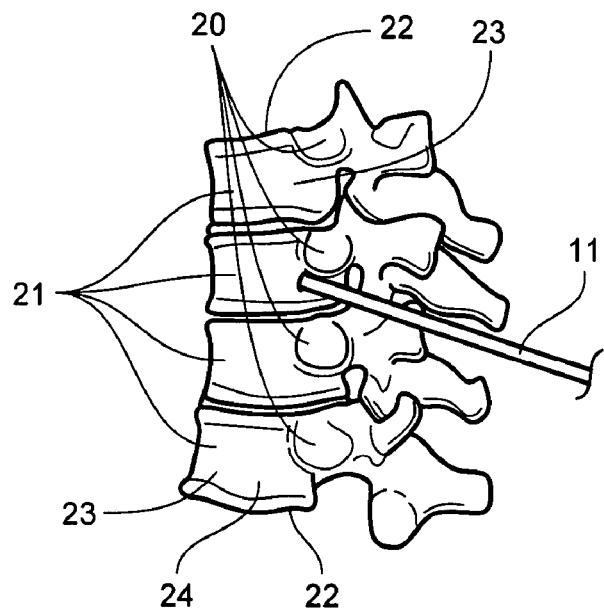
FIG. 2 is an elevation (lateral) view of several human vertebrae, with a delivery cannula establishing a path to a vertebral body of one of the vertebrae.
Figure 3:
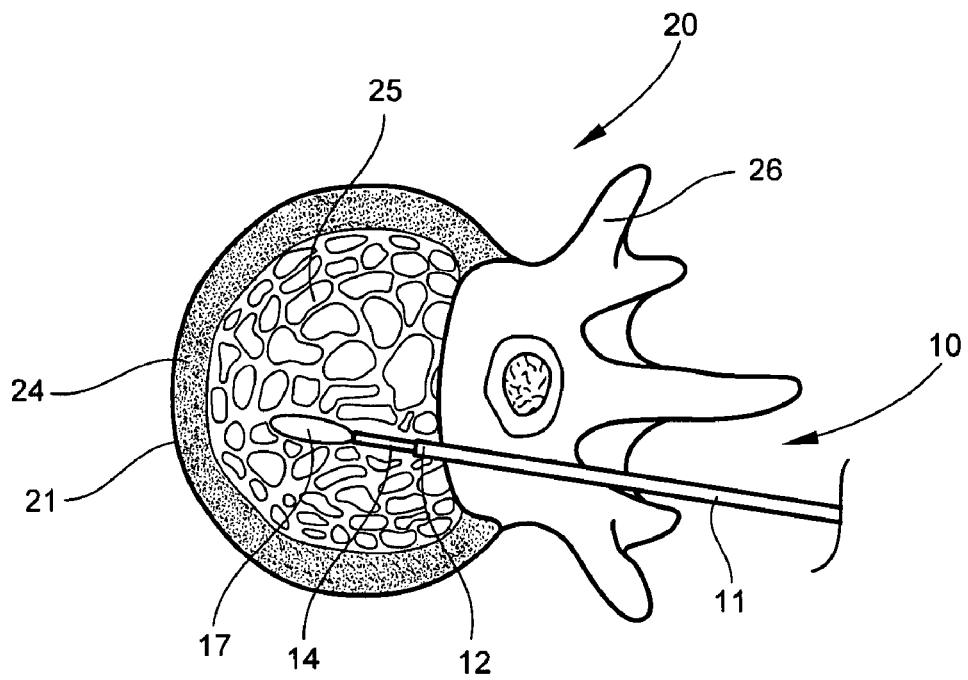
FIG. 3 is a plan (coronal) view of a human vertebra being accessed by a delivery cannula, with portions of the vertebra removed to reveal cancellous bone within a vertebral body.

Referring now to FIGS. 2 and 3, an elevation (lateral) view of several human vertebrae 20 is shown, with the delivery cannula 11 establishing a percutaneous path along its elongated axis 52 to a vertebral body 21 of one of the several vertebrae 20. The vertebral body 21 extends on the anterior (i.e., front or chest) side of the vertebrae 20. The vertebral body 21 comprises an exterior formed from compact cortical bone 24. Cortical bone (24) is defined as bone consisting of, or relating to, cortex, or outer layer of a bony structure. The cortical bone 24 encloses an interior volume of reticulated cancellous 25, or spongy, bone (also called medullary bone or trabecular bone).

Due to various traumatic or pathologic conditions, such as osteoporosis, a vertebral body 21 can experience a vertebral compression fracture (VCF). In such conditions, cancellous bone 25 can be compacted, causing a decrease in height of the vertebra 20. In a VCF in particular, vertebral height tends to be lost in the anterior region of the vertebral body 21. The user of the system 10 may utilize it to provide a cavity, or void, within the vertebral body 21, and to restore height to the vertebral body 21 lost when a fracture occurred.

The upper and/or the lower surface of a vertebral body 21 with which an intervertebral disc has contact is defined as a vertebral body endplate 22. Each vertebral body 21 has a top, or superior, endplate 22 and a bottom, or inferior, endplate 22. Vertebral body endplates 22 comprise cortical bone 24. The perimeters of the endplates 22 are reinforced due to the generally perpendicular proximity to the cortical bone 24 in the walls 23 of the vertebral body. However, the tissue inside the vertebral body 21 is soft cancellous bone 25. As a result, the middle portion of the endplates 22 may not be well supported anatomically and may thus be the most susceptible to deformation and collapse.

The vertebral body 21 is in the general shape of an oval disc. As FIGS. 2 and 3 show, access to the interior volume of the vertebral body 21 can be achieved, for example, by drilling an access portal through a rear side of the vertebral body 21 (a postero-lateral approach). The portal for the postero-lateral approach enters at a posterior side of the vertebral body 21 and extends anteriorly into the vertebral body 21. Alternatively, access into the interior 33 volume of a vertebral body 21 can be accomplished by drilling an access portal through one or both pedicles 26 of the vertebra 20. This is known as a transpedicular approach.

Some embodiments of the present invention, for example, the system 10 can be configured to be used, for example, in a kyphoplasty procedure. Kyphoplasty is a minimally invasive surgical procedure for reducing a vertebral fracture and restoring height to an injured or diseased vertebra 20. In a kyphoplasty procedure, after a cavity is formed in a vertebral body 21, a bone filler material can be introduced into the resulting cavity to provide increased height and stability to the vertebra 20.

Applications and uses of embodiments of the bone support and/or barrier devices 13 can vary depending on various clinical factors. For example, some embodiments of bone support devices 13 and/or systems 10 of the present invention may be utilized to repair a fractured bony structure from the interior 33 of a bone. Alternatively, or in addition, some embodiments may be implanted as a preventative measure to help reduce the incidence of fractures in certain patients.

In some embodiments, the bone support and/or barrier device 13 may be implanted into the interior of a bone alone. In other embodiments, the bone support and/or barrier device 13 may be implanted into the interior of a bone in combination with a bone filler material. For example, the expandable body 17, such as a balloon kyphoplasty bone tamp, may be utilized to create a void in the vertebral body 21. After the void is created, the bone support and/or barrier device 13 may be inserted into and deployed in the vertebral body 13. Once the device 13 is in a desired position, a bone cement can be injected into the void to fill the rest of the void.

In some clinical situations, expansion of the expandable body 17 may create enough lift to move the superior endplate 22 in relation to the inferior endplate 22, thereby restoring height to the collapsed vertebral body 21. However, once the expandable body 17 is removed, the superior endplate 22 may partially or completely collapse from its restored height. In such a situation, the bone support device 13 may be implanted in the vertebral body 21 to maintain the restored height of the vertebral body 21.

In some embodiments, the bone support device 13 may be inserted into and deployed in the interior of the vertebral body 21 along with the expandable body 17 such that once height restoration is achieved and the expandable body 17 is retracted from the vertebral body 21, the bone support device 13 can remain inside the vertebral body 21 to provide support to the endplate 22. In other embodiments, once a void is created and the height of the vertebral body 21 is restored, the expandable body 17 can be removed from the vertebral body 21. After the expandable body 17 is removed, the bone support device 13 can be inserted to the interior of the vertebral body 21 through the same percutaneous path as the expandable body 17. Once in a desired position inside the vertebral body 21, the bone support device 13 can be deployed to maintain the endplates 22 in a position of restored height and prevent the endplates 22 from migrated back towards each other. In such an embodiment, the bone support device 13 can be adapted to expand with a lifting force on the endplates 22 sufficient to restore the height of the vertebral body 21 between the endplates 22.

In some clinical situations, it may be desirable to avoid the use of a bone filler material. Thus, in some embodiments, the bone support device 13 may be deployed in the vertebral body 21 without injection of a bone filler material, or cement. In other embodiments, once the bone support device 13 is in position in the vertebral body 21, a bone filler material may be injected into the vertebral body 21 to provide further structural support to the endplates 22 and vertebral body 21.

In some embodiments, the bone support device 13 can be configured such that once deployed inside the vertebral body 21, it can transfer a load, or force, 34 exerted downward along the axis of the superior endplate 21 towards the vertebral body walls 23, thereby supporting the superior endplate 22. In other embodiments, the bone support device 13 can be configured such that once deployed inside the vertebral body 21, it can transfer the load 34 exerted downward along the axis of the superior endplate 22 towards the inferior endplate 22 and thus provide support to the superior endplate 22. In still other embodiments, the bone support device 13 can be configured such that once deployed inside the vertebral body 21, it can support the superior endplate 22 by transferring an axial load 34 exerted on the superior endplate 21 towards both the vertebral body walls 23 and the inferior endplate 22.

FIG. 3 shows a vertebra 20 being accessed by the system 10 according to an embodiment of the present invention. The vertebra 20 is shown with portions removed to reveal cancellous bone 25 within the vertebral body 21. The user of the system 10 may slide the elongate member 14 and attached components axially, or lengthwise, along the elongated axis 52, within the delivery cannula 11 to deliver the components to the targeted treatment site.

In a kyphoplasty procedure, or other vertebral body repair procedure, the elongate member 14 can have attached to its distal end 16 a device for creating a void, or cavity, in the cancellous bone 25 of the vertebral body 21. As shown in FIG. 3, the void-creating device can be an expandable body 17, such as an inflatable balloon, as shown in FIG. 3. In some embodiments, other apparatus and methods can be used to create a void within a vertebral body 21 or other bony structure. The user may rotate the elongate member 14, and thereby the expandable body 17, to position the expandable body 17 for selective expansion in the target treatment area.

After the expandable body 17 is moved beyond the distal end 12 of the delivery cannula 11, the expandable body 17 may be expanded from a contracted state to an expanded state to provide a cavity within the cancellous bone 25. The expandable body 17 may be expanded by movement of a flowable material, for example, normal saline, through the hollow elongate member 14 and into the interior of the expandable body 17. Embodiments of an expandable body 17 can move the superior and/or inferior endplates 22 of a vertebral body 21 toward a more normal anatomical position to restore height. In this manner, the outer dimensions of the vertebral body 21 can be maintained an/or restored. Once a desired void has been created, the expandable body 17 may be contracted by withdrawing the flowable material out of the expandable body 17 through the hollow lumen of the elongate member 14. The elongate member 14 and the contracted expandable body 17 may then be withdrawn through the delivery cannula 11.

In a minimally invasive procedure, an embodiment of the bone support and/or barrier device 13 can be inserted percutaneously to a treatment site in a collapsed, or closed, undeployed configuration. Once the undeployed bone support and/or barrier device 13 is in a desired position in the interior 33 of a bone, the device 13 can be expanded to a deployed configuration. The bone support and/or barrier device 13 can be expanded, or deployed, to its deployed configuration with various deployment mechanisms. One such mechanism for deploying the bone support and/or barrier device 13 from its undeployed configuration can be the expandable body 17, which may be, for example, an inflatable balloon.

The expandable body 17 may be attached to the distal end 16 of the elongate member 14 and inserted through the lumen of the delivery cannula 11 to the target site. The expandable body 17 can then be expanded, such as by inserting a flowable material through the hollow elongate member 14 and into the interior of the expandable body 17. Expanding the expandable body 17 inside the undeployed bone support and/or barrier device 13 can cause the bone support and/or barrier device 13 to expand outwardly from its undeployed configuration into its deployed configuration. In addition, in some embodiments, expanding the bone support and/or barrier device 13 outwardly can cause the device 13 to be moved to a desired position within a bony structure. In some embodiments, the bone support and/or barrier device 13 can be moved outwardly by other deployment mechanisms, for example, a hydraulic mechanism, by mechanical actuation, or by other suitable mechanisms and/or interfaces.

In some embodiments of the present invention, the bone support and/or barrier device 13 can be delivered to a target area, for example, in the interior 33 of a bone, simultaneously with the expandable device 17. In such embodiments, the bone support and/or barrier device 13 can be deployed with the expandable body 17 from a first, collapsed state or configuration to a second, expanded state or configuration in the target area. In other embodiments, a void can be created with the expandable body 17 and the expandable body 17 removed. Then, the bone support and/or barrier device 13 can be delivered through the delivery cannula 11 to the target area and deployed with an expandable device 17 or other deployment mechanism.

After the expandable body 17 is removed, a material or filler, such as a bone cement, may be used to fill the void provided by the system 10. Use of a filler material may be beneficial in certain treatment areas, for example, in a vertebra 20 where the system 10 is used to restore height to a vertebral body 21. Such a bone filler material can distribute an axial load 34 (as shown in FIG. 6) transferred from the vertebral body 21 surfaces to the hardened filler material, ultimately strengthening the spine.

Embodiments according to the present invention are not limited in application to human vertebrae 20, and may be used to provide support to bony structures within other parts of a living or non-living organism. In certain embodiments, the system 10 can be utilized in various locations within the human body, depending upon the treatment goals as well as the anatomy of the targeted bone. For example, embodiments of a bone support device 13 and/or system 10 may be utilized in the treatment of areas within the body other than the vertebra 21, including, for example, the ribs, the femur, the radius, the ulna, the tibia, the humerus, the calcaneus, or the spine.

One illustrative embodiment of the bone support device is shown in FIGS. 4-6B. As shown in FIG. 6A, the bone support and/or barrier device 13 can comprise a deployed configuration having an arch, or dome, shape 44 similar to the shape of an opened umbrella.

Figure 6A:
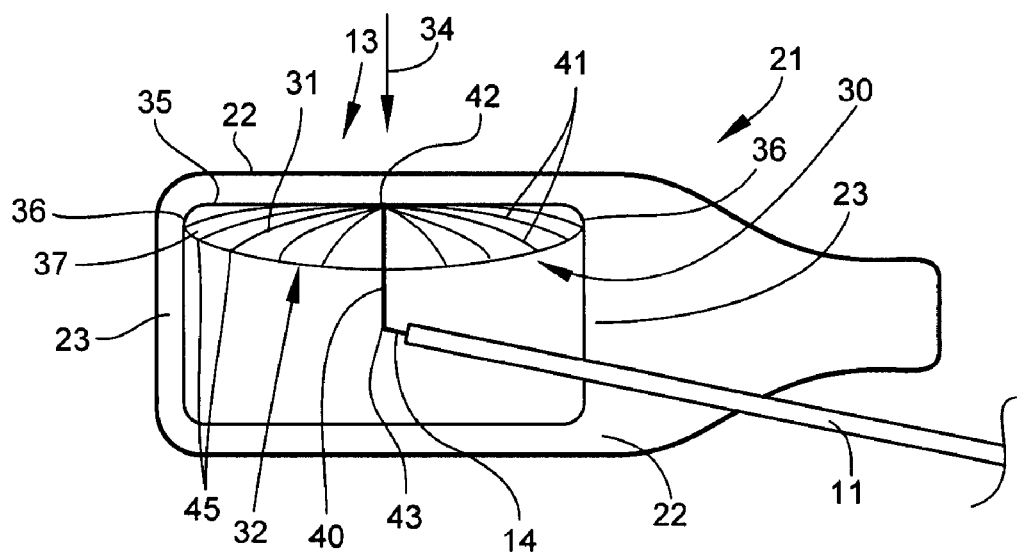
FIG. 6A is a cross-sectional view of a vertebral body showing the bone support device in FIG. 4, fully deployed in contact with an endplate and walls of the vertebral body in an embodiment of the present invention.

After the delivery cannula 11 has been percutaneously inserted to a target area in an interior body region, such as in a vertebral body 21, the bone support and/or barrier device 13 can be delivered to the target area through the delivery cannula 11. As shown in FIG. 6A, the bone support and/or barrier device 13 can be pivotably attached in a collapsed, undeployed configuration to the distal end 16 of the elongate member 14 and delivered through the delivery cannula 11 to the target site. In some embodiments, the handle 50 can be attached to the proximal end 15 of the elongate member 14 outside a patient's body. The handle 50 can include a mechanism that can be used to deploy the bone support device 13 into a deployed configuration.

The bone support and/or barrier device 13 may be delivered to a target surgical site using other access devices. For example, in some embodiments, the bone support and/or barrier device 13 can be delivered into a target bony structure using a conventional bone filler device (not shown). Alternatively, the bone support and/or barrier device 13 may be attached to the distal end of a modified curette (not shown) and delivered on the modified curette through the delivery cannula 11 to the target site.

As shown in the embodiments in FIGS. 4-6B, the implantable structure 30 of the bone support and/or barrier device 13 can comprise a central rod 40 pivotably attached about a pivot 43 to the distal end 16 of the elongate member 14. A plurality of support members 41 can be pivotably attached to the distal end 42 of the central rod 40 such that the support members 41 can be extended outwardly in a circular pattern. In the deployed configuration, the plurality of outwardly extending support members 41 can form an arch, or dome shape 44.

When used in a vertebral body repair procedure, the bone support and/or barrier device 13 can be positioned in a desired location within the vertebral body 21, for example, in a void created in the center of the vertebral body 21 between the endplates 22. Once the bone support and/or barrier device 13 is in position, a first deployment mechanism 51 in the handle 50 can be actuated to pivot, or "cock," the bone support device 13, for example, approximately 90 degrees relative to the longitudinal axis 52 of the elongate member 14 to point the distal end 42 of the central rod 40 toward an endplate 22. (See FIG. 5.) A second deployment mechanism 53 in the handle 50 can then be actuated to extend the support members 41 outwardly from the central rod 40 so as to deploy the device 13 into its operative configuration. (See FIGS. 6A-B.) In some embodiments, the first (rod pivoting) deployment mechanism 51 can be actuated by partially depressing the trigger portion of the handle 50. The second (support member extending) deployment mechanism 53 may be actuated by further depressing the trigger portion of the handle 50. Other mechanisms for deploying the bone support and/or barrier device 13 may be used. For example, ratcheted or spring-loaded mechanisms may be used to help deploy the bone support and/or barrier device 13. In some embodiments, the bone support and/or barrier device 13 can comprise a shape memory material that can facilitate deployment of the device.

Some embodiments of the bone support and/or barrier device 13 can include a mechanism to release the device 13 from the distal end 16 of the elongate member 14 after it has been deployed and positioned in a desired position in a vertebral body 21. For example, one end of the bone support and/or barrier device 13 can include threads and can be threaded onto mating threads on the distal end 14 of the elongate member 14. When the device 13 is in position, the elongate member 14 can be rotated so as to "unscrew" the elongate member 14 from the bone support and/or barrier device 13 and release the device 13 into the vertebral body 21. In another embodiment, the bone support and/or barrier device 13 can be fit snugly over the distal end 16 of the elongate member 14. When the device 13 is in position, the device 13 can be urged off the end 16 of the elongate member 14 by slightly retracting the elongate member 14 such that the proximal edge of the device 13 contacts the distal edge 12 of the delivery cannula 11, thus releasing the device 13 into the vertebral body 21. Alternative release mechanisms adapted to release the central rod 40 from the elongate member 14 can be employed.

Some embodiments of the bone support and/or barrier device 13 can comprise an implantable structure 30 having an outer surface 31, an inner surface 32, a first bone contact portion 35, and a second bone contact portion 36. As shown in the embodiments in FIGS. 6A-B, in its deployed configuration, the implantable structure 30 of the bone support and/or barrier device 13 can be positioned so that the outer surface 31 of the arch-shaped, outwardly extending support members 41 contacts the center, or near the center, of the endplate 22. That is, at least a portion of the outer surface 31 of the outwardly extending support members 41 can comprise the first bone contact portion 35. When the outer surface 31 of the structure 30 is in contact with the endplate 22, the distal ends 42 of the outwardly extending support members 40 can be positioned in contact with cortical bone 24 about the perimeter of the vertebral body 21. Thus, the distal ends 42 about a perimeter of the outwardly extending support members 41 can comprise the second bone contact portion 36 of the device 13.

With the outer surface 31 of the device 13 in contact with the endplate 22 and the distal ends 42 of the support members 41 in contact with the vertebral body walls 23, the axial load 34 placed on the endplate 22, particularly in the center of the endplate 22, can be transferred through the device 13 to the stronger cortical bone 24 in the vertebral body walls 23. As a result, the bone support device 13 can spread out the load 34 on the endplate 22 and distribute it more evenly across a larger area and against more rigid structures (cortical bone 24) in the vertebral body 21. If the axial load 34 on the endplate 22 reaches an amount such that the endplate 22 begins to deform, the pressure against the bone support device 13 can cause the device 13 to place more spreading force on the support members 41. As the support members 41 spread farther from the center of the device 13 in a flattening manner due to the load 34 transferred from the endplate 22, the perimeter of the device 13 can be pushed more tightly against the cortical bone 24, which can provide support against further deformation of the endplate 22.

In some embodiments, the bone support and/or barrier device 13 can be positioned in a vertebral body 21 to deploy, or expand, upwardly toward a superior endplate 22 or to expand downwardly toward an inferior endplate 22. The elongate member 14 can be rotated to position the bone support and/or barrier device 13 so that it is oriented in either the upward or downward position. In other embodiments, the device 13 can include two or more sets of support members 41. One set of support members 41 can be deployed upwardly into contact with the superior endplate 22, and another set of support members 41 can deployed downwardly into contact with the inferior endplate 22.

In other embodiments, each of a plurality of bone support devices 13 can be adapted in the deployed configuration to support a separate portion of the bone. For example, a first bone support device 13 can be inserted into a vertebral body 21 and deployed into contact with one endplate 22. Following deployment of the first bone support device 13, a second bone support device 13 can be inserted into the vertebral body 21 and deployed into contact with the opposite endplate 22.

Some embodiments of a bone support device 13 of the present invention can provide support or protection to an endplate 22 that may be weakened due to a disease process, for example, increased porosity due to osteoporosis. Such a weakened endplate 22 may be reinforced in the middle portion of the endplate 22 and thus help protect against possible vertebral compression fractures. In other embodiments, the bone support device 13 can provide support to an already compromised anatomical structure, such as a vertebral body endplate 22, while an adjacent void is being created, during reconstruction of nearby structures, and/or while a bone filler material is inserted and cured in the void.

In some embodiments, the bone support and/or barrier device 13 can be utilized in combination with a bone filler material that can be inserted into a vertebral body void adjacent the device 13. In some embodiments, the bone filler material, or cement, can provide structural support adjacent the bone support and/or barrier device 13 for protecting the integrity of the vertebral body 21. Alternatively, the bone support device 13 can be utilized without a bone filler material.

The bone support device 13 can be made from various surgical materials suitable for use in an interior body region. For example, the bone support device 13 can be made from materials such as titanium, a shape memory material such as Nitinol, stainless steel, and/or polymers that are sufficiently strong to support a bony structure. In various embodiments, the bone support device 13 can have a thickness sufficient to provide desired load support to an endplate 22 to prevent deformation or collapse of the endplate 22. For example, the device 13, including the support members 41, can have a thickness in the range of about 1-5 mm. The desired thickness of the device material can depend on a number of factors, including, for example, whether the device 13 is to be permanently implanted, whether a bone filler material is to be used with the device 13, whether the device 13 has a lateral dimension sufficient to span an entire endplate 22 or less than the entire endplate 22, etc.

In some embodiments, the bone support and/or barrier device 13 can have a barrier material 37, for example, as shown in FIG. 6, connecting the support members 41. Such a span of barrier material 37 can provide additional support to an endplate 22 or other bony structure. The barrier material 37 can be adapted to prohibit substantially all flow of bone filler material from the inner surface 32 of the deployed device 13 to the outer surface 31 of the device 13. In this manner, the device 13 can help prevent leakage of bone filler material through a compromised bone adjacent the device 13. The barrier material 37 can comprise Teflon® (polytetrafluoroethylene), Dacron®, or other implantable, biocompatible material. In an embodiment, the barrier material 37 can comprise an open weave pattern adapted to reduce, but not necessarily stop, the flow of bone filler material from the inner surface 32 to the outer surface 31 of the device 13.

In certain embodiments, the barrier material 37 can have a porosity sufficient to allow nutrients to diffuse through the material 37 so as to reach the interior of the vertebral body 21. Alternatively, the barrier material 37 can be a biodegradable material that can provide additional support to an endplate 22 for a limited period of time, after which the material degrades and is absorbed into surrounding tissue. Such a biodegradable material can include nutrients that can promote bone growth.

In some embodiments, the barrier material 37 can be a solid tubular material, for example, a thin polymeric elastic material such as latex, placed about the exterior of the support members 41. In an alternative embodiment, the barrier material 37 can be sheet material, such as sheets of a thin polymeric elastic material, attached and sealed to adjacent support members 41. The barrier material 37 can be attached between each pair of adjacent support members 41, or between less than each pair of adjacent support members 41. The barrier material 37 can be attached to the device 13 by, for example, sealing the material 37 to the support members 41 with radio frequency or laser sealing or by other suitable mechanisms.

In an embodiment, the barrier material 37 may comprise a nanocomposite plastic material. Nanocomposites include a resin matrix and a nano-sized reinforcing filler material. Commercially available nano-fillers include clays, silicas, and ceramics. Nanocomposites and nano-fillers are available commercially from the Foster Corporation, Putnam, Conn. These fillers are small enough to improve the strength of the resin matrix so as to provide a strong barrier material 37, while allowing the material 37 to be extruded as a thin structure.

Some embodiments of the bone support and/or barrier device 13 can be shaped and sized to fit a void created in the interior of a bone. In certain embodiments, the bone support and/or barrier device 13 can be sized so as to span across substantially all of an endplate 22 when in a fully expanded configuration. Alternatively, the bone support and/or barrier device 13 can be sized to span less than substantially all of an endplate 22 when fully expanded. For example, the fully expanded device 13 can be sized to cover approximately half or approximately one-third of the lateral dimensions of an endplate 22. Such smaller embodiments of the bone support device 13 can be used individually to provide protection to a particular portion of an endplate 22. Alternatively, a plurality of embodiments of the bone support and/or barrier device 13 having expanded, or deployed, dimensions less than that of the lateral dimensions of an endplate 22 can be used together to provide protection for the entire endplate 22. It may be desirable to use embodiments of bone support and/or barrier devices 13 having less than the full dimensions of an endplate 22 when access for delivery of a larger bone support device 13 to the vertebral body 21 may be difficult. Rather than attempting to insert one larger bone support and/or barrier device 13, two smaller bone support and/or barrier devices 13 may be inserted, for example, one device 13 through each pedicle of a vertebra 20 or via a different surgical approach.

Figure 5:
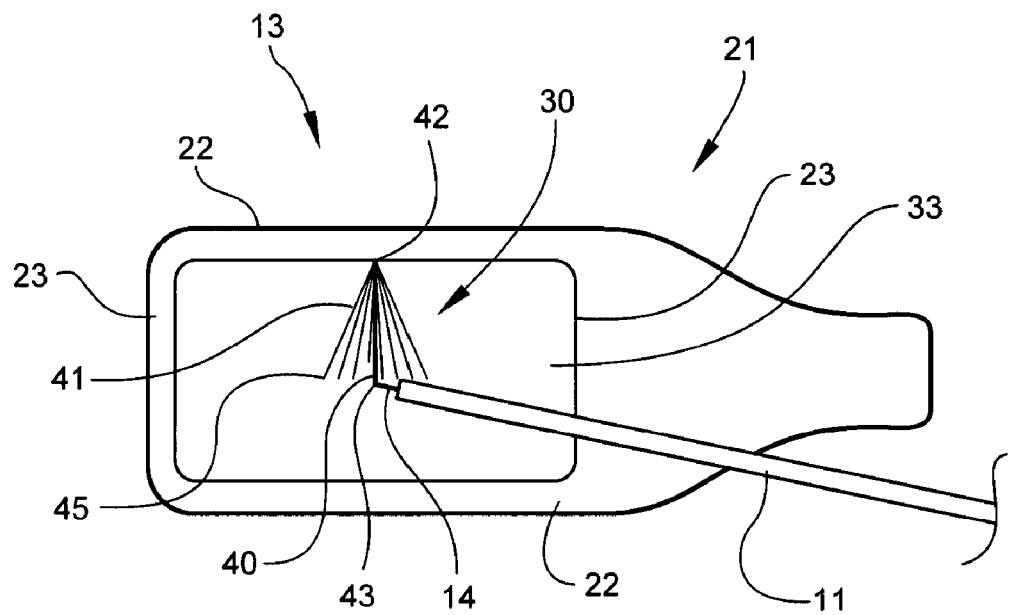
FIG. 5 is a cross-sectional view of a vertebral body showing the bone support device in FIG. 4, pivoted toward an endplate in an embodiment of the present invention.

The embodiment of the bone support device 13 in FIGS. 5 and 6 can have varying vertical dimensions, or heights, when in its fully deployed configuration. For example, the bone support device 13 can have a domed or arched configuration 44 such that the height at least initially gradually decreases from the center of the support members 41 toward the perimeter of the support members 41. As pressure from the endplate 22 is transferred to the device 13, the height at the center of the device 13 can decrease as the support members 41 spread out to a larger angle relative to the central rod 40. In another embodiment, the bone support device 13 can have an initial fully deployed configuration that is essentially flat about the entire lateral dimension of the device 13.

Figure 6B:
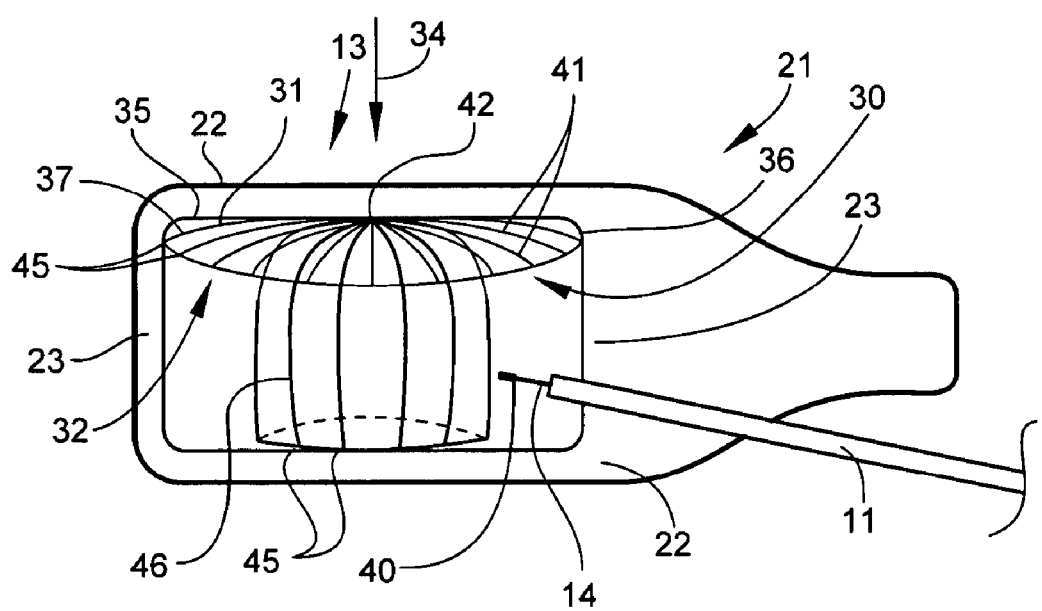
FIG. 6B is a cross-sectional view of a vertebral body showing an embodiment of the bone support device having two sets of support members, one set of support members fully deployed in contact with an endplate and walls of the vertebral body and the other set of support members fully deployed in contact with both the superior and inferior endplates, in another embodiment of the present invention.

FIG. 6B illustrates an alternative embodiment of the bone support device 13 shown in FIG. 6A. As shown in the embodiment in FIG. 6B, the umbrella-shaped bone support device 13 can include the first set of support members 41 as described herein and a second set of support members 46. When the bone support device 13 is in its deployed configuration, the second set of support members 46 can extend downward from the distal end 42 of the central rod 40 at a more acute angle than the first set of support members 41. The second set of support members 46 can extend the entire distance between the superior endplate 22 and the inferior endplate 22 in the interior of the vertebral body 21. With the outer surface 31 of the bone support device 13 in contact with one of the endplates 22, for example, the superior endplate 22, and the distal ends 42 of the first set of support members 41 in contact with the vertebral body walls 23, the axial load 34 placed on the superior endplate 22 can be transferred through the device 13 to the stronger cortical bone 24 in the vertebral body walls 23. In addition, with the distal ends 42 of the second set of support members 46 in contact with the opposite, inferior endplate 22, the load 34 placed on the superior endplate 22 contacting the outer surface 31 can be transferred through the device 13 to the stronger cortical bone 24 in the inferior endplate 22. As a result, the bone support device 13 can spread out the load 34 on the first endplate 22 and distribute it more evenly across a larger area and against more rigid structures (cortical bone 24) in the vertebral body 21.

Another embodiment of the bone support device 13 is shown in FIGS. 7-13. In such an embodiment, the bone support device 13 can comprise an implantable structure 30 comprising a frame 60 having an outer ring 61 and a series of cross-members 62 each extending from one point on the outer ring 61 to another, generally opposite point on the ring 61. The configuration of the outer ring 61 and the cross-members 62 can form an open weave, or grid, pattern. An open weave pattern has the advantage of allowing nutrient transfer to the adjacent intervertebral disc.

One side of the grid of cross-members 62 can comprise the outer surface 31 of the implantable structure 30, and the opposite side of the grid of cross-members 62 can comprise the inner surface 32. The outer surface 31 of the cross-members 62 can comprise the first bone contact portion of the device 13 that can contact a first bone portion in the interior of a bone, for example, an endplate 22 in a vertebral body 21.

The outer ring 61 can comprise the second bone contact portion that can contact a second bone portion, for example, cortical bone 24 about the perimeter of the vertebral body 21. In this manner, a load 34 placed on the first portion of the bone can be transferred through the implantable structure 30 to the second portion of the bone, thereby supporting the first bone portion.

Figure 7:
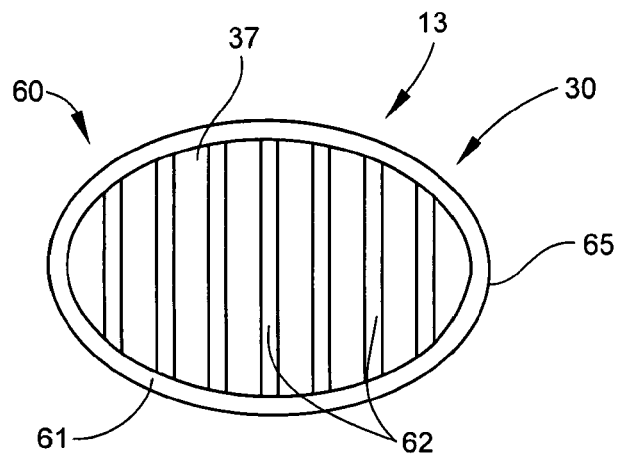
FIG. 7 is a view of a bone support device comprising an implantable frame structure having an outer ring and cross-members in another embodiment of the present invention.
Figure 8:
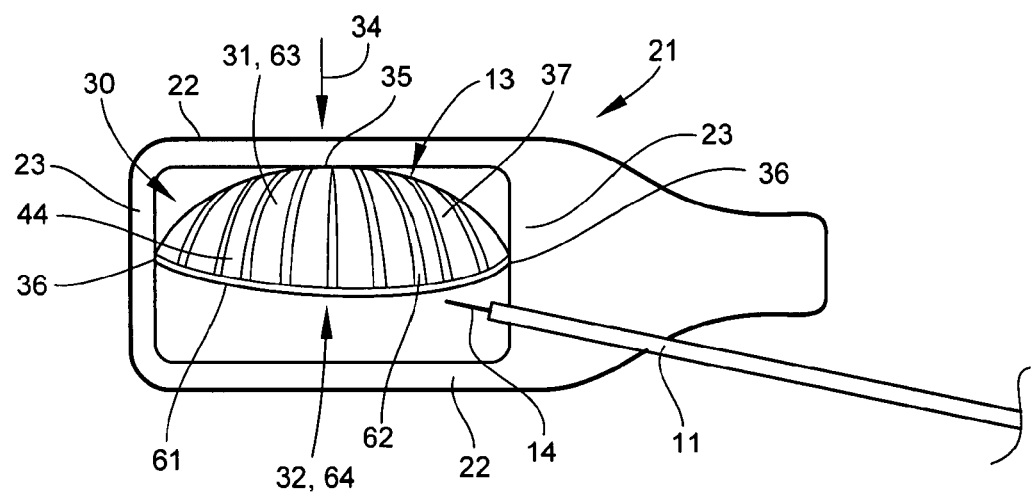
FIG. 8 is a cross-sectional view of a vertebral body showing a bone support device comprising a dome-shaped implantable frame structure having an outer ring and cross-members that is fully deployed in contact with an endplate and walls of the vertebral body in an embodiment of the present invention.

Embodiments of the bone support device 13 having the outer ring 61 and a grid of cross-members 62 can have various configurations. For example, as shown in FIG. 7, the outer ring 61 can have a circular or oval shape 65. In some embodiments, the bone support device 13 comprising the outer ring 61 and a grid of cross-members 62 can be configured to have an arched "dome" shape 66, as shown in FIG. 8, when the device 13 is deployed inside an internal body region. Such a dome shape 66 can aid in the transfer of the axial load 34 from the endplate 22 by providing a biased contact between the arched outer surface 31, or convex surface 63, of the cross-members 62 and the endplate 22. In addition, such a dome shape 66 can allow the perimeter of the outer ring 61 to engage cortical bone 24 along the vertebral walls 23 in a biased manner. As a result, the load 34 can be transferred from the supported endplate 22 to cortical bone 24 in another vertebral body structure so as to provide a greater resistance to the load stress in the endplate 22. In an embodiment in which the outer ring 61 does not initially engage one or more surfaces of the vertebral walls 23, as pressure from the endplate 22 is exerted on the upper, convex surface 63 of the cross-members 62, the remainder of the device 13 may spread outwardly toward and into contact with cortical bone 24 in the walls of the vertebral body 21. In this manner, support from the cortical bone 24 in the vertebral body walls 23 can stop further inward movement of the endplate 22. The transfer of load stress from the endplate 22 can help protect the endplate 22 from undergoing a compression fracture or from experiencing extension of an existing fracture.

Figure 9:
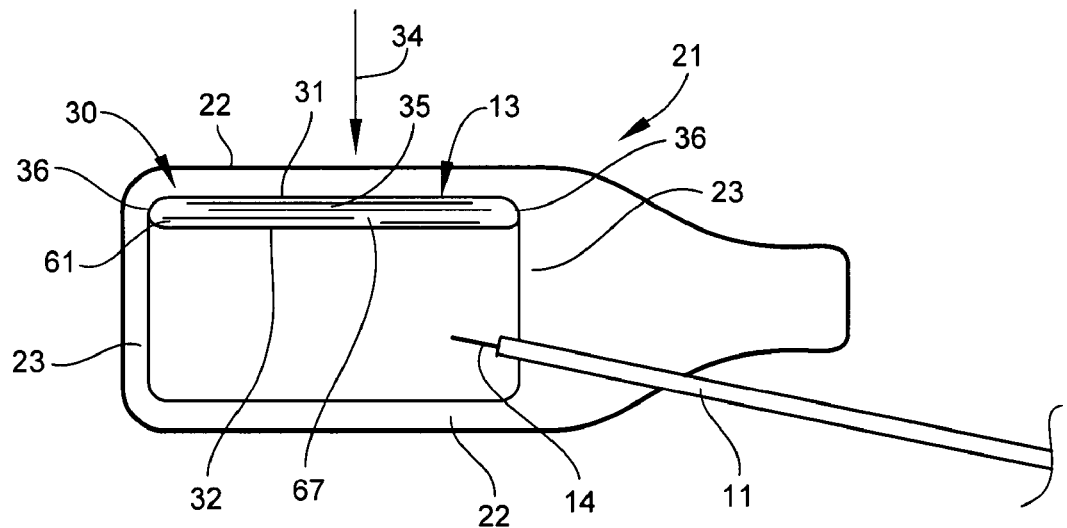
FIG. 9 is a cross-sectional view of a vertebral body showing a bone support device comprising a flat-shaped implantable frame structure having an outer ring and cross-members that is fully deployed in contact with an endplate and walls of the vertebral body in an embodiment of the present invention.

Another embodiment of the bone support device 13 comprising the outer ring 61 and cross-members 62 can have an essentially flat configuration 67, as shown in FIG. 9. In such an embodiment, the device 13 can be delivered into the vertebral body 21 and deployed so as to be positioned into contact with both an endplate 22 and cortical bone 24 in the walls 23 of the vertebral body 21. That is, the device 13 may be deployed into direct contact with the endplate 22 without further positioning (such as rotating approximately 90 degrees as with the embodiment shown in FIGS. 4-6). In such a flat configuration 67, load pressures 34 exerted on the endplate 22 can be transferred through the structure of the device 13 to the cortical bone 24 in the vertebral body walls 21.

Figure 10:
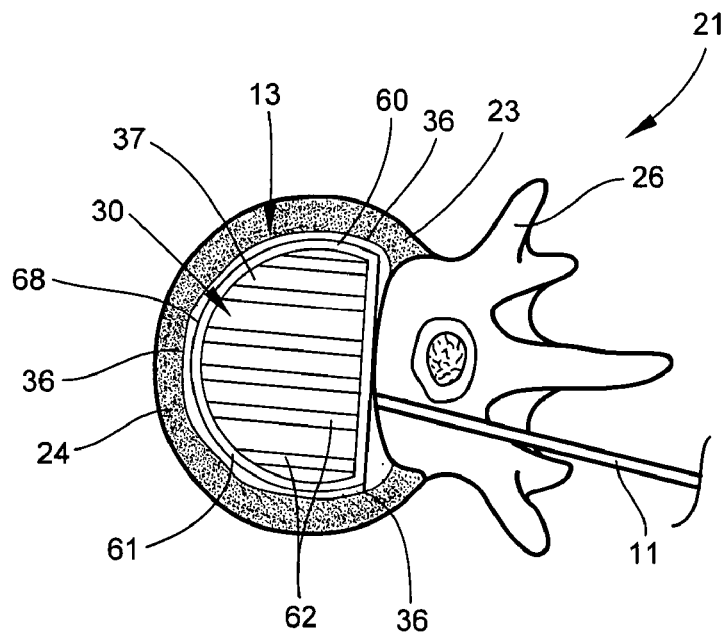
FIG. 10 is a plan (coronal) view of a human vertebra with portions of the vertebra removed showing a bone support device comprising a semi-circular-shaped implantable frame structure having an outer ring and cross-members that is fully deployed in contact with walls of the vertebral body in an embodiment of the present invention.

In another embodiment, as shown in FIG. 10, the outer ring 61 can be in the shape of a semi-circle 68 with one side of the semi-circle 68 being a flat portion of the outer ring 61 and the remainder of the semi-circle 68 being an arcuate, circumferential edge connected to the ends of the flat portion of the outer ring 61. In this configuration, the cross-members 62 can extend from the flat side of the outer ring 61 to the arcuate, circumferential edge of the outer ring 61. A semi-circular configuration 68 may be advantageous for conforming to the interior of certain bony structures, such as a vertebral body 21.

Some embodiments of the bone support device 13 comprising the outer ring 61 and cross-members 62 can have other configurations that are suitable for displacing axial load pressures 34 on an endplate 22 to other bony structures (such as cortical bone 24). The design, shape, or configuration of the bone support device 13 comprising the outer ring 61 and cross-members 62 can vary depending on a number of factors, including, for example, the type of anatomical structure intended for support and protection, the materials used to make the device 13, the type of deployment apparatus, the location of the target site, whether access to the target site is via open surgery or by minimally invasive techniques, and others.

In certain embodiments, the bone support device 13 comprising the outer ring 61 and cross-members 62 can be sized so as to span across substantially all of an endplate 22 when in a deployed configuration. Alternatively, the bone support device 13 can be sized to span less than substantially all of an endplate 22 when fully deployed. In some embodiments, a plurality of the bone support devices 13 can be used together to provide support to particular portions of the endplate 22 or other bony structure(s).

Figure 22A:
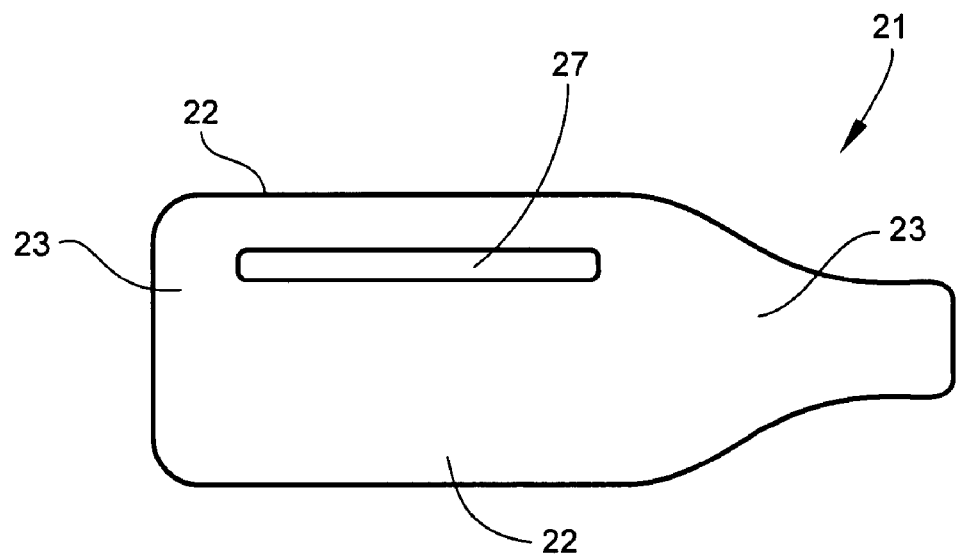
FIGS. 22A-B are cross-sectional views of a vertebral body showing a vertebral body access in the vertebral body wall in an embodiment of the present invention.
Figure 22B:
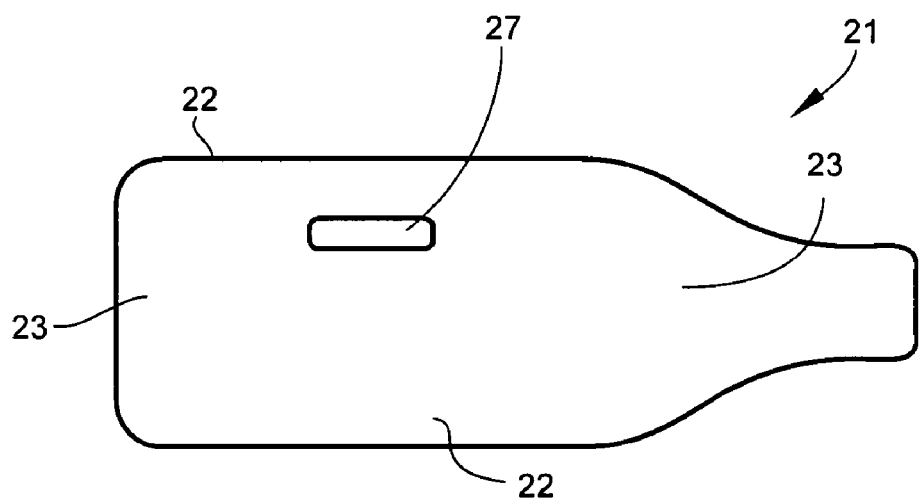

In some embodiments, the bone support device 13 can be delivered into the interior of the vertebral body 21 through various locations in the vertebral body wall 23 relative to the endplate 22. For example, embodiments of the bone support device 13 can be delivered into the vertebral body 21 interior at a location in the vertebral body wall 23 near the endplate 22 such that the bone support device 13 can be deployed adjacent the endplate 22. As shown in FIGS. 22A and 22B, in certain embodiments, a vertebral body access 27 can be made in the vertebral body wall 23 near the endplate 22. The delivery cannula 11 can be inserted through the vertebral body access 27, and the bone support device 13 can be delivered through the delivery cannula 11 into the interior of the vertebral body 21.

When the vertebral body access 27 is located in the vertebral body wall near the endplate 22, as shown in FIGS. 22A and 22B, the bone support device 13 can be delivered into the vertebral body 21 interior in a position adjacent the endplate 22. In certain embodiments, the bone support device 13 may be delivered through the vertebral body access 27 such that the bone support device 13 can be positioned in contact with both the endplate 22 and cortical bone 24 in the walls 23 of the vertebral body 21. That is, the device 13 may be deployed into direct contact with the endplate 22 without further positioning. As shown in FIGS. 22A and 22B, the dimensions of the vertebral body access 27 can vary. For example, the vertebral body access 27 may extend along the majority of the lateral side of the vertebral body 21, as in the embodiment in FIG. 22A. In another embodiment, the vertebral body access 27 may extend along a shorter portion, for example, less than half, of the lateral side of the vertebral body 21, as in the embodiment in FIG. 22B.

Embodiments of the bone support device 13 comprising the outer ring 61 and cross-members 62 can comprise various materials, including, for example, shape memory materials such as Nitinol or shape-memory plastics. The bone support device 13 can comprise materials that impart suitable rigidity to provide structural support to the target bony structure.

In some embodiments, the bone support and/or barrier device 13 comprising an outer ring and cross-members can have a barrier material 37, for example, as shown in FIGS. 7, 8, and 10, connecting the cross-members 62. Such a span of barrier material 37 may provide additional support to an endplate 22 or other bony structure. The barrier material 37 can be adapted to prohibit substantially all flow of bone filler material from the inner surface 32 (such as the inner concave surface of the dome-shaped device in FIG. 8) of the deployed device 13 to the outer surface 31 of the device 13. In this manner, the device 13 can help prevent leakage of bone filler material through a compromised bone adjacent the device 13.

In an embodiment, the barrier material 37 can comprise an open weave or mesh design adapted to reduce, but not necessarily stop, the flow of bone filler material from the inner surface 32 to the outer surface 31 of the device 13. In such an embodiment, the bone barrier device can reduce the flow of bone filler material from the inner surface 32 to the outer surface 31 of the device 13, while allowing the flow of some bone filler material through the barrier material 37, which can contact and bond with a bony structure adjacent the outer surface 31 of the device 13. In yet another embodiment, the bone support and/or barrier device 13 can include through holes in either the cross-members 62 or the barrier material 37, or both, so that the bone filler material can penetrate through the device 13 to fill the space in the void both adjacent the inner surface 32 and adjacent the outer surface 31 of the device 13.

Some embodiments of the bone support device comprising an outer ring and cross-members can be inserted into an interior body region such as a vertebral body via a minimally invasive technique. For example, the delivery cannula 11 having a hollow lumen can be percutaneously inserted to the interior of a vertebral body. The bone support device 13 can be releasably attached in an undeployed configuration to the distal end 16 of the elongate member 14. The elongate member 14 and the attached bone support device 13 can be inserted through the lumen of the delivery cannula 11 into the vertebral body. When the bone support device 13 is in a desired position in the vertebral body, the device can be deployed into a deployed configuration into contact with the endplate, vertebral body walls, and/or other bony structures in the vertebral body. Then, the bone support device 13 can be released from the elongate member 14, and the elongate member 14 and delivery cannula 11 removed from the vertebral body.

Some embodiments of the bone support device 13 comprising an outer ring and cross-members can be collapsed from a deployed, or expanded, configuration to an undeployed, or collapsed, configuration have a geometry sized and shaped so as to fit through the lumen of the delivery cannula 11.

Figure 12:
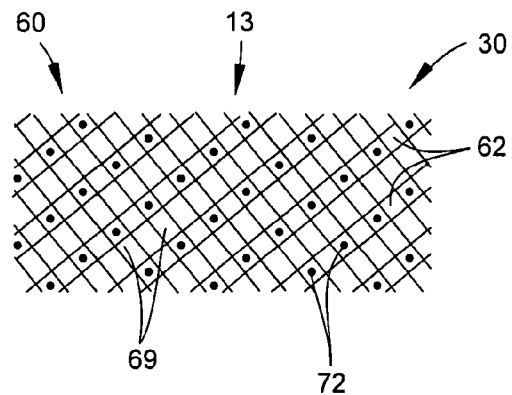
FIG. 12 is a view of cross-members of a bone support device comprising an implantable frame structure showing the cross-members having pivotable intersections with other cross-members in an embodiment of the present invention.
Figure 13:
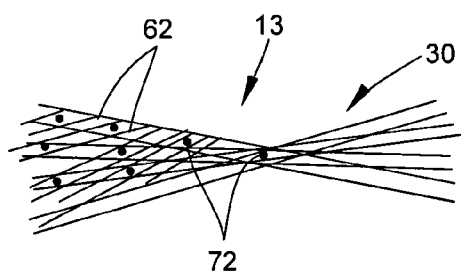
FIG. 13 is a view of the cross-members in FIG. 12, in which the cross-members have been collapsed into an undeployed configuration by pivoting at the cross-member intersections in an embodiment of the present invention.

In some embodiments, the cross-members 62 can be configured to extend in different directions relative to other cross-members 62. For example, in some embodiments, as shown in FIGS. 7, 8, 10, and 11, the cross-members 62 can be configured to extend from one position to another position on the outer ring 61 in a substantially parallel relationship 69 to each other. In other embodiments, for example, as shown in FIGS. 12 and 13, the cross-members 62 can be configured to extend so as to intersect with other cross-members 62 and form an open weave pattern. The cross-members 62 can be configured in any pattern suitable for providing structural support to a bony structure, such as a vertebral body endplate 22, and that is amenable to being percutaneously inserted into an interior body region in an undeployed, or collapsed, configuration.

Figure 11:
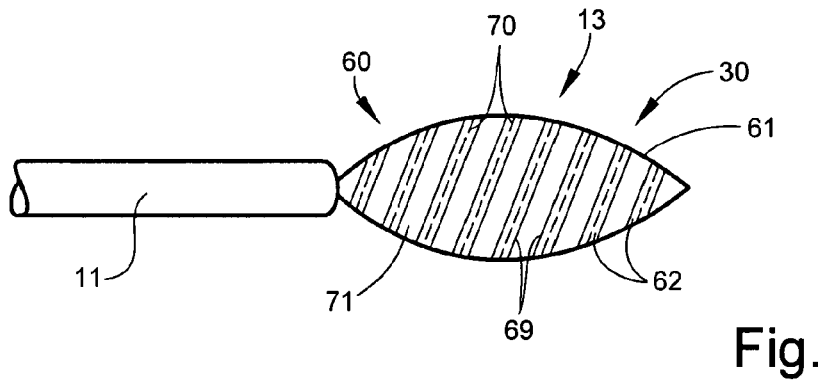
FIG. 11 is a side view of a bone support device comprising an implantable frame structure having an outer ring and cross-members in an elongated, undeployed configuration in an embodiment of the present invention.

In one embodiment, as shown in FIG. 11, the bone support device 13 comprising the outer ring 61 and cross-members 62 can be extended, or "stretched," along its longitudinal axis so as to form a more narrow, elongated configuration 71 that can be inserted through the delivery cannula 11. FIGS. 12 and 13 show another embodiment of a cross-member design, in which the cross-members 62 can have an expanded, deployed configuration in which the cross-members 62 are aligned at approximately right angles relative to each other in an open weave, or "X-shaped" pattern. The cross-members 62 can be pivotably connected at intersections 72 at which they cross. By mechanically pulling on the ends of the cross-members 62, the cross-members 62 can be pivoted about the intersections 72 such that the cross-members 62 can collapse to a nearly parallel relationship 69. FIG. 13 shows the cross-members 62 in an intermediate position between a deployed configuration as in FIG. 12 and a fully collapsed, undeployed configuration. In this manner, the bone support device 13 having the outer ring 61 and cross-members 62 can be collapsed into an undeployed configuration so as to fit through the lumen of the delivery cannula 11 for insertion into an interior body region. Once the bone support device 13 is inserted into the interior body region, such as the vertebral body 22, a force can be exerted against at least one of the ends of the collapsed cross-members 62 so as to mechanically push, or expand, the cross-members 62 back into their original deployed configuration.

Expansion of the bone support and/or barrier device 13 from an undeployed configuration to a deployed configuration may be facilitated by using a shape memory material, such as Nitinol or shape-memory plastics, in the device 13. When the device 13 is in a desired position in a vertebral body 22, heat from the patient's body can cause the shape memory material to deploy into its expanded deployed configuration.

Figure 14A:
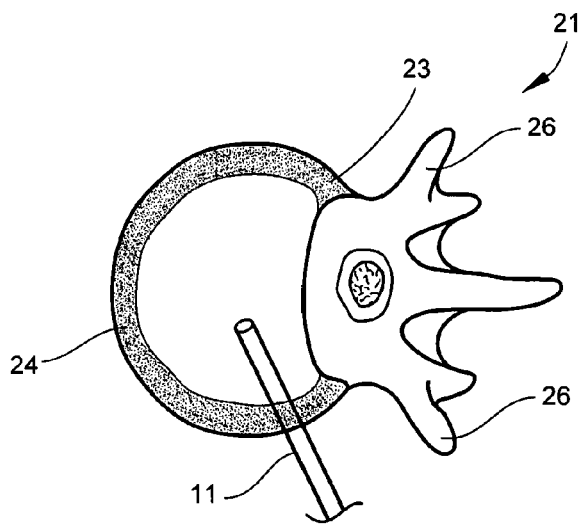
FIGS. 14A-C are plan (coronal) views of a human vertebra with portions of the vertebra removed and showing a delivery cannula inserted into the interior of the vertebral body using an extra-pedicular approach in an embodiment of the present invention.
Figure 14B:
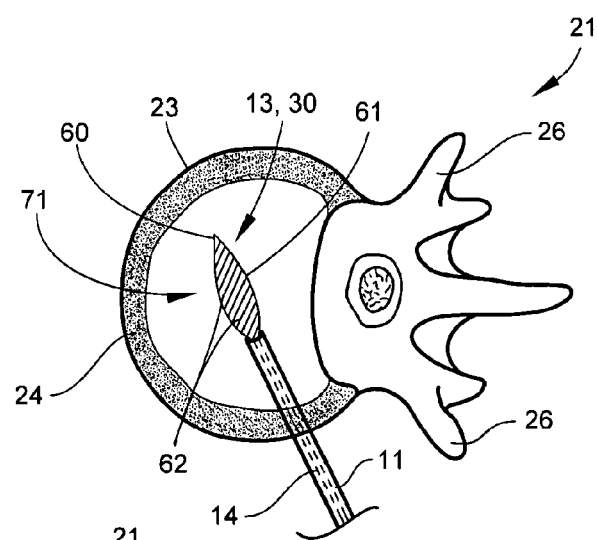
Figure 14C:
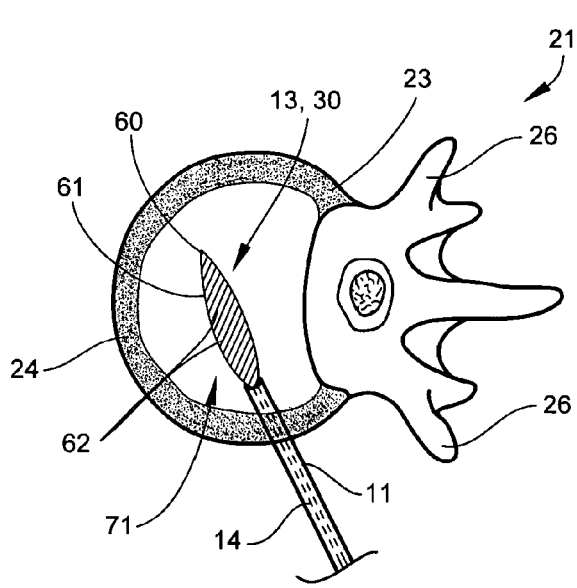

In some embodiments, the implantable bone support and/or barrier device 13 can be delivered to the interior of the vertebral body 21 by a trans-pedicular approach, as shown in FIGS. 5-6, 8-10, 15, and 17-19. In an alternative embodiment, as shown in FIGS. 14A-14C, the bone support and/or barrier device 13 can be delivered to the interior of the vertebral body 21 by an extra-pedicular approach. As shown in FIG. 14A, in an extra-pedicular approach, the delivery cannula 11 may be inserted into and positioned within the vertebral body 21 from a position lateral to one of the vertebral body pedicles 26. As an example, FIG. 14B illustrates the delivery cannula 11 in place in the vertebral body 21 using an extra-pedicular approach. The elongate member 14 can be inserted through the delivery cannula 11 such that the bone support and/or barrier device 13 attached to the distal end 16 of the elongate member 14 can be deployed inside the vertebral body 21. The embodiment of the bone support and/or barrier device 13 illustrated in FIGS. 14B and 14C is the embodiment of the device 13 comprising the frame 60 having the outer ring 61 and the cross members 62 shown in FIGS. 7, 8, and 11. As shown in FIG. 14B, the bone support device 13 can have the elongated configuration 71 while being inserted through the delivery cannula 11, and may be extended beyond the distal end 16 of the delivery cannula 11 into the interior of the vertebral body 21. As the delivery cannula 11 is retracted from its previous position shown in FIG. 14B, toward the vertebral body wall 23, as shown in FIG. 14C, the bone support device 13 may be fully extended beyond the delivery cannula 11 such that the device 13 can be positioned into a fully deployed configuration. The bone support device 13 may be fully deployed in various manners, such as using a mechanical deployment mechanism, for example, the deployment mechanism actuated by the handle 50 shown in FIG. 4, or by self-deploying mechanisms, for example, as may be facilitated with the use of shape-memory material(s) in the device 13. The bone support device 13 shown in FIGS. 14A-14C delivered into the interior of the vertebral body 21 may be fully deployed into a configuration similar to that shown in FIG. 8.

An extra-pedicular insertion approach may be useful for delivery of the bone support and/or barrier device 13 having dimensions that require a relatively large percutaneous insertion path into the vertebral body 21. For example, in some surgical procedures in which only an expandable body such as a balloon is inserted into the vertebral body 21, the delivery cannula 11 may be relatively small and the percutaneous insertion path can likewise be relatively small. A transpedicular insertion approach may accommodate such a relatively small delivery cannula 11. For procedures that include implanting an embodiment of the bone support and/or barrier device 13, the delivery cannula 11 may need to be larger than the delivery cannula 11 required for delivering only an expandable body. In such procedures, a trans-pedicular approach may not be desirable for inserting such a larger delivery cannula 11. Accordingly, an extra-pedicular insertion approach may better accommodate insertion of a relatively larger delivery cannula 11 (and bone support and/or barrier device 13, for example) into the interior of the vertebral body 21. In addition, an extra-pedicular approach may allow insertion of the bone support and/or barrier device 13 in a position closer to and/or more closely aligned with, the endplate 22, for example, as shown in FIG. 9.

Figure 17:
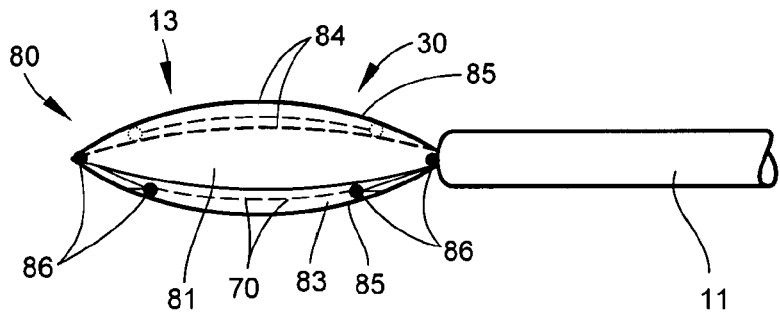
FIG. 17 is a view of the bone support device in FIG. 15, in which the frame members have been pivoted about the pivot joints into a collapsed, undeployed configuration in an embodiment of the present invention.
Figure 18:
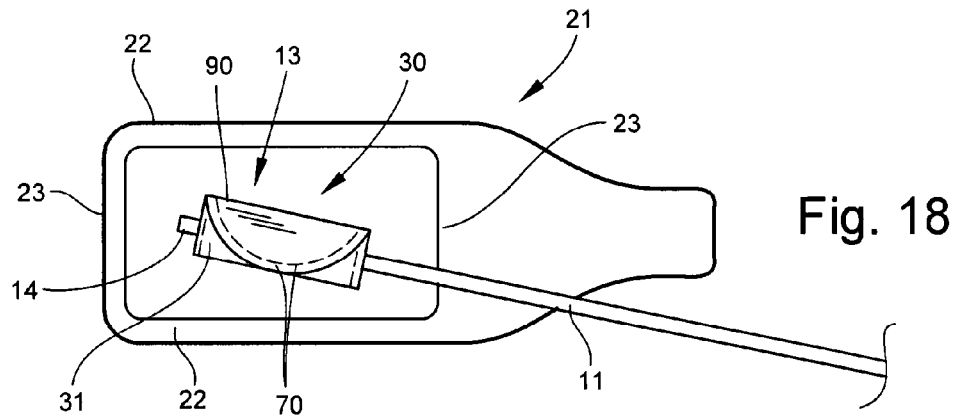
FIG. 18 is a cross-sectional view of a vertebral body showing a bone support device comprising a disc of material wrapped about an elongate member in an undeployed configuration in an embodiment of the present invention.

As shown in FIGS. 11, 17, and 18, the bone support and/or barrier device 13 can include one or more radiopaque markers 70 that can be visualized under fluoroscopy. Radiopaque is defined as being opaque to radiation and especially x-rays. Fluoroscopy is defined as examination by means of a fluoroscope. A fluoroscope is a device equipped with a fluorescent screen on which the internal structures of an optically opaque object, such as the human body, may be viewed as shadowy images formed by the differential transmission of x-rays through the object.

The radiopaque markers 70 can be arranged in a radiopaque marking pattern that can be configured to allow for radioscopically visualizing the positioning and orientation of the device 13 in the interior body region during deployment. As a result, a non-radiopaque contrast medium can be used, for example, to expand the expandable body 17, thereby eliminating the risk of exposing a patient to a radiopaque contrast agent.

In some embodiments, the radiographic marking pattern can provide essentially an outline of the shape of the bone support and/or barrier device 13 when expanded. Thus, in addition to fluoroscopically monitoring the bone support and/or barrier device 13 as it is being deployed, when the device 13 is expanded to its deployed configuration, the periphery of the device 13, and thereby the outer contact points of the bone support and/or barrier device 13 onto tissue in the interior body region can be visualized radioscopically.

In some embodiments of the present invention, in addition to the bone support and/or barrier device 13, at least a portion of the delivery cannula 11, elongate member 14, and/or expandable body 17 may comprise one or more radiographic material(s) and/or markers 70. In this manner, positioning of the components used to deliver and deploy the bone support and/or barrier device 13 can be visualized radioscopically during use. As such, the user can monitor positioning of the entire bone support device system 10 and any differences in positioning of one component relative to the other component.

Radiopaque markers 70 can be made from radiopaque materials. Examples of radiopaque materials include stainless steel, platinum, gold, calcium, tantalum, barium sulfate, tantalum, tungsten, bismuth subcarbonate, and other metals.

Figure 15:
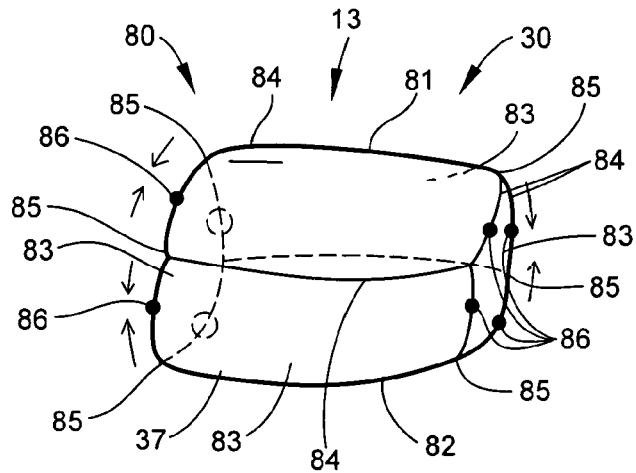
FIG. 15 is a perspective view of a bone support device comprising an implantable six-sided frame structure having pivotable joints in at least some of the frame members in an embodiment of the present invention.
Figure 16:
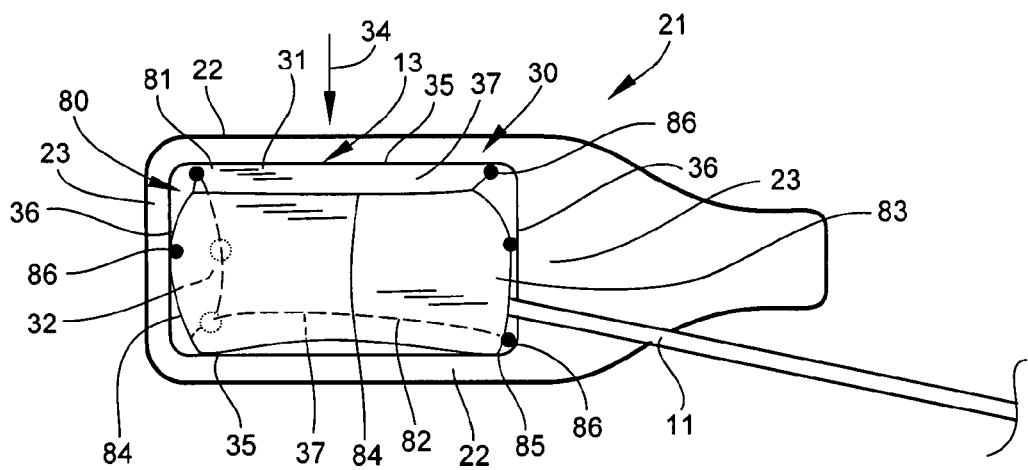
FIG. 16 is a cross-sectional view of a vertebral body showing the bone support device in FIG. 14, in a fully deployed configuration in contact with an endplate and walls of the vertebral body in an embodiment of the present invention.

FIGS. 15-17 illustrate another embodiment of a bone support and/or barrier device 13. As shown in this embodiment, the device 13 can be configured to guide and or control the distribution of bone filler material injected into the interior of a bone. In some embodiments, the bone support and/or barrier device 13 can comprise an implantable sheet of barrier material 37 having six sides comprising a top 81, a bottom 82, and four rounded faces 83, as shown in FIGS. 15-17. The faces 83 can be generally perpendicular to the top 81 and the bottom 82 of the sheet of material 37.

The six-sided sheet of barrier material 37 can have the appearance of a rounded cube-like structure. The rounded nature of the top 81, bottom 82, and faces 83 of the sheet of barrier material 37 allows the sheet of barrier material 37 to more closely fit the contours of a void created inside a bony structure, such as a vertebral body 21. In its deployed configuration, the outer surfaces 31 of the top 81 and bottom 82 of the sheet of barrier material 37 may be positioned into contact with selected portions of the interior of the bone, for example, the superior and inferior endplates 22 in a vertebral body 21, and the outer surfaces 31 of the faces 83 may contact the vertebral body walls 23. In other embodiments, the sides of the sheet of barrier material 37 may be positioned so as to be free of contact with the interior of the bone into which it is delivered. With the sheet of barrier material 37 of the bone barrier device in a desired position, the distribution of bone filler material injected into the interior of the vertebral body 21 can be guided and/or controlled. In this manner, the sheet of barrier material 37 can prohibit substantially all flow of bone filler material from the inner surface 32 (inside) of the material 37 of the deployed device 13 to the outer surface 31 of the material 37. In this manner, the device 13 can help prevent leakage of bone filler material through a compromised bone adjacent the barrier material 37.

In an embodiment, the sheet of barrier material 37 can comprise an open weave pattern adapted to reduce, but not necessarily stop, the flow of bone filler material from the inner surface 32 to the outer surface 31 of the device 13. For example, the sheet of barrier material 37 may comprise an open weave, mesh, and/or through hole configuration that is sufficiently fine to contain most of the flowable bone cement injected inside the barrier material 37 to prevent leakage outside the vertebral body 21 and still allow enough bone cement to penetrate the barrier material 37 so as to form a bond with the adjacent cortical bone 24.

In certain embodiments, the barrier material 37 can be a contiguous sheet of material. The barrier material 37 can comprise Teflon®, Dacron®, or similar biocompatible material. In some embodiments, the top 81, bottom 82, and/or faces 83 of the sheet of barrier material 37 of the bone barrier device 13 can comprise a barrier material that can allow flow of fluids and nutrients through the material.

In some embodiments, the sheet of barrier material 37 can comprise one or more sides of the bone barrier device 13. As such, the bone barrier device 13 can be utilized to selectively restrict movement of a flowable material in various directions. By restricting the area into which a flowable material can move while being injected and cured, spread of the flowable material out of a void or bony structure, such as through a structurally compromised endplate 22 and/or vertebral body side wall 23, into undesired areas can be minimized or prevented.

In various embodiments of a such a six-sided bone barrier device 13, from one to five sides of the device 13 can be open (without barrier material 37), all sides can be open, or no sides can be open. An open side of the bone barrier device 13 can be oriented toward a portion of a bony structure, such as a vertebral body wall 23, so that when bone cement is injected into the void inside the vertebral body 21, the bone cement can flow into contact with the vertebral body wall 23 adjacent the open side. In this manner, the bone cement can "interdigitate" with the cortical bone 24 in the exposed wall 23 of the vertebral body 21 to form a bond with the bone 24, thereby providing a more stable support to the vertebral body 21.

In embodiments in which one to five sides are open without barrier material 37, the bone barrier device 13 can be oriented so that open side(s) are facing compromised portion(s) of the endplate(s) 22 and/or vertebral body wall(s) 23 so as to contain flowable bone cement when it is injected into the void inside the vertebral body 21. In embodiments in which no sides are open, bone cement can be prevented from contacting any cortical bone 24 surface inside the vertebral body 21. Although in embodiments with no open sides the bone cement cannot form a bond with cortical bone 24, the presence of the cured bone cement can provide structural support to the vertebral body 21. Embodiments of a totally closed-sided bone support device 13 may be desirable in a procedure to repair a vertebral compression fracture in which the endplates 22 and a large portion of the vertebral wall 23 are compromised and there is risk of bone cement leakage from multiple locations about the vertebral body 21.

In certain embodiments, the bone support and/or barrier device 13 comprising a sheet of barrier material 37 may have less than six sides. For example, the bone support and/or barrier device 13 may have from one to five sides. In each of the embodiments of the device 13 having from one to six sides, the sheet of barrier material 37 can provide a mechanism by which the distribution of bone filler injected into or adjacent the barrier material 37 can be guided and/or controlled.

During a procedure to repair a vertebral compression fracture, bone filler material, such as a bone cement, may be inserted into the vertebral body 21 to provide structural support to the vertebral body 21. In situations in which the fracture compromises the integrity of the endplate 22 or the wall 23 of the vertebral body 21, there may be a risk that the bone cement can leak from the compromised bone. Bone cement leakage can produces symptoms, including painful irritation of a nerve root emerging from the spinal column, degeneration of the walls of major vessels, and possibly degeneration of the compromised endplate(s) 22. Thus, some embodiments of the bone support and/or barrier device 13 of the present invention can provide the advantage of preventing leakage of bone cement into undesired areas.

As shown in FIGS. 15-17, the top 81, bottom 82, and four rounded faces 83 of the six-sided bone support and/or barrier device 13 can be formed about an implantable frame 80. The frame 80 can be configured such that the faces 83 can be generally perpendicular to the top 81 and the bottom 82 of the device 13. The frame 80 can include a plurality of frame members 84. Each of the members 84 can be connected at each end to two other of the frame members 84 at joints 85 between the sides. In some embodiments, the barrier material 37 can be a contiguous sheet of material connected to the frame members 84. In other embodiments, a separate sheet of the barrier material 37 can be attached to one or more sides of the device 13.

In some embodiments, the bone support and/barrier device 13 can be positioned inside the bone into which it is delivered so that when the frame 80 is in its fully deployed position, the sheet of barrier material 37 can be free of contact with the bone. In other embodiments, in the fully deployed configuration, the outer surface 31 of at least one side of the frame 80 can contact the first bone portion 35 inside a bony structure, and the outer surface 31 of at least another side can contact the second portion 36 of the bone so as to provide support to the first bone portion. For example, the outer surfaces 31 of the top 81 and bottom 82 of the frame 80 can be positioned in contact with the superior and inferior endplates 22 in a vertebral body 21, and the outer surfaces 31 of the faces 83 can contact the vertebral body walls 23. As such, the axial load 34 placed on the endplate 22 can be transferred from the endplate 22 through the frame 80 to the vertebral body walls 23, thereby providing support to the endplate 22. In each of these embodiments, the sheet of barrier material 37 can provide a mechanism by which the distribution of bone filler injected into or adjacent the barrier material 37 can be guided and/or controlled.

In some embodiments, the frame members 84 on at least opposing sides of the frame 80 can include pivot joints 86 near the center of the frame members 84. The pivot joints 86 allow the frame members 84 to pivot at the pivot joints 86 so as to allow the bone support device frame 80 to be collapsed to an undeployed configuration. For example, as shown in FIG. 17, in an embodiment in which the frame members 84 on opposite ends of the frame 80 include pivot joints 86, exerting a force on those frame members 84 can cause the top and bottom portions of those frame members 84 to pivot about the pivot joints 86 and fold into a generally parallel relationship with each other. As a result, the ends of the frame 80 having the pivot joints 86 can be collapsed so that the top 81 and bottom 82 of the frame 80 are adjacent each other. The frame members 84 on the ends of the top 81 and bottom 82 of the frame 80 (which include pivot joints 86) can be pivoted about those pivot joints 86 such that opposite sides of those frame members 84 can be folded together. Pivoting the ends of the top 81 and bottom 82 of the frame 80 can cause the remaining non-adjacent sides to be collapsed adjacent each other. As a result, the frame 80 can be collapsed into an undeployed configuration for delivery into an interior body region. In addition, the pivot joints 86 can provide the sides of the frame 80 with a sufficient degree of flexibility to allow the sides to conform to possibly uneven surfaces inside a void in a vertebral body 21.

In embodiments of the six-sided bone support and/or barrier device 13 comprising an implantable frame 80, one or more sides of the frame 80 and sheet of barrier material 37 can be open. In embodiments in which all sides are open, the bone barrier device 13 includes no barrier material 37, and bone cement can flow into contact with all cortical bone 24 surfaces inside the vertebral body 21. In embodiments of a totally open-sided frame 80, the frame members 84 can provide support to the endplates 22 as well as to the vertebral body walls 23.

Some embodiments of the bone support and/or barrier device 13 having from one to six sides can be inserted into an interior body region such as a vertebral body 21 via a minimally invasive technique. For example, the delivery cannula 11 having a hollow lumen can be percutaneously inserted to the interior 33 of the vertebral body 21. The bone support and/or barrier device 13 can be releasably attached in an undeployed configuration to the distal end 16 of the elongate member 14. The elongate member 14 and the attached bone support and/or barrier device 13 can be inserted through the lumen of the delivery cannula 11 into the vertebral body 21. When the bone support and/or barrier device 13 is in a desired position in the vertebral body 21, the device 13 can be deployed into a deployed configuration into contact with the endplate 22, vertebral body walls 23, and/or other bony structures in the vertebral body 21. Then, the bone support and/or barrier device 13 can be released from the elongate member 14, and the elongate member 14 and delivery cannula 11 removed from the vertebral body 21.

The bone support and/or barrier device 13 can be expanded to a desired deployed configuration using various apparatus and techniques. For example, some embodiments of the bone support and/or barrier device 13 may be expanded into the deployed configuration with the expandable body 17, such as an inflatable balloon tamp. The expandable body 17 can be pre-positioned inside the bone support and/or barrier device 13 and delivered to the target bony structure at the same time the bone support device 13 is delivered. Alternatively, the bone support and/or barrier device 13 can be first delivered to the target bony structure, after which the expandable body 17 can be delivered through the delivery cannula 11 to inside the bone support and/or barrier device 13 in the target bony structure. From inside the bone support and/or barrier device 13, the expandable body 17 can be expanded to thereby expand the bone support and/or barrier device 13 to its deployed configuration.

In some embodiments, the expandable body 17 can be utilized to position and/or orient the bone support and/or barrier device 13 in the bony structure. For example, the bone support and/or barrier device 13 can be partially expanded with the expandable device 17 and oriented into a desired position such that a closed side of the device 13 comprising barrier material 37 is facing the portion(s) of the surrounding structures into which it is desired to prevent flow of a flowable material. The expandable device 17 can then be further expanded to fully deploy the bone support and/or barrier device 13. With the bone support and/or bather device 13 in place, the expandable body 17 can be deflated and removed. In other embodiments, the bone support and/or barrier device 13 can be oriented to a desired position relative to areas within a bony structure in which it has been delivered in other manners and using other apparatus. Once the device 13 is fully deployed and positioned, the device 13 can be released from the elongate member 14. The void can then be filled with a flowable bone filler material through the delivery cannula 11.

In some embodiments, the collapsed, undeployed bone support and/or barrier device 13 can be covered with a sheath (not shown) during delivery through the delivery cannula 11 to the target site. Such a sheath can help maintain the device 13 in its undeployed configuration during delivery into the target bony structure. Once the bone support and/or barrier device 13 is in position in the bony structure, the sheath can be removed from around the bone support and/or barrier device 13 and retracted through the delivery cannula 11. When the sheath is removed from about the bone support and/or barrier device 13 inside the target bony structure, the device 13 can be expanded to its deployed configuration.

In certain embodiments, the bone support and/or barrier device 13 can comprise a shape memory material, such as Nitinol. The sheath can help maintain the device 13 comprising shape memory material in its undeployed configuration during delivery into a target bony structure. When the bone support and/or barrier device 13 comprising a shape memory material is delivered to the target site inside a sheath and the sheath is removed from the bone support and/or barrier device 13, the device 13 can expand to it deployed configuration without further manipulation. That is, the normal temperature of the patient's body can warm the shape memory material sufficiently to cause the bone support and/or barrier device 13 to expand to its deployed configuration.

The bone support and/or barrier device 13 comprising the six-sided frame 80 can include radiopaque markers 70, as shown in FIG. 17. The radiopaque markers 70 can be arranged in a radiopaque marking pattern that can be configured to allow for radioscopically visualizing the positioning and orientation of the device 13 in the interior body region. For example, the radiopaque markers 70 can be arranged to provide essentially an outline of one or more of the sides of the bone support and/or barrier device 13 when expanded. In this manner, the user can directly monitor positioning of those sides of the bone support and/or barrier device 13 relative to various portions of the bony structure while deploying the device 13.

In certain embodiments, the bone support and/or barrier device 13 comprising the frame 80 having one to six sides can be sized so as to span across substantially all of a vertebral body endplate 22 when in its deployed configuration. Alternatively, the bone support and/or barrier device 13 can be sized to span less than substantially all of an endplate 22 when fully deployed. In some embodiments, a plurality of the bone support and/or barrier devices 13 can be used together to provide support to particular portions of the endplate 22 or other bony structure(s).

Figure 19:
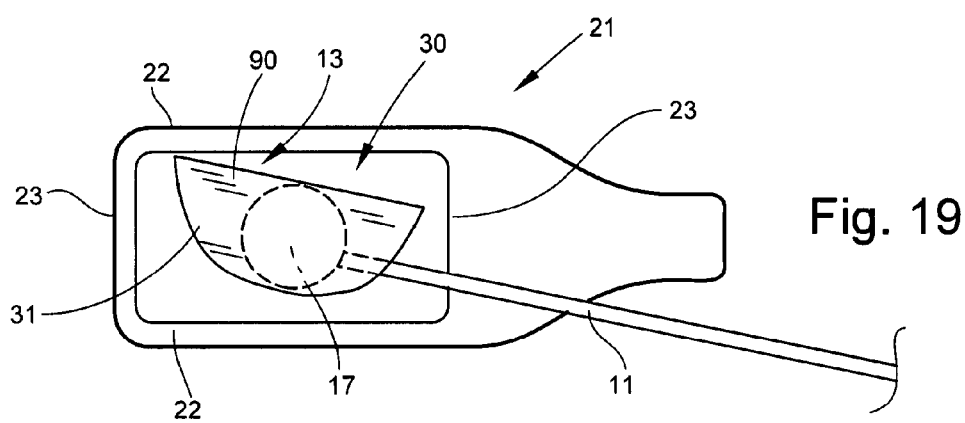
FIG. 19 is a cross-sectional view of a vertebral body showing the bone support device in FIG. 18, in which the disc of material is partially unwrapped by expansion of an expandable body inside the disc in an embodiment of the present invention.
Figure 20:
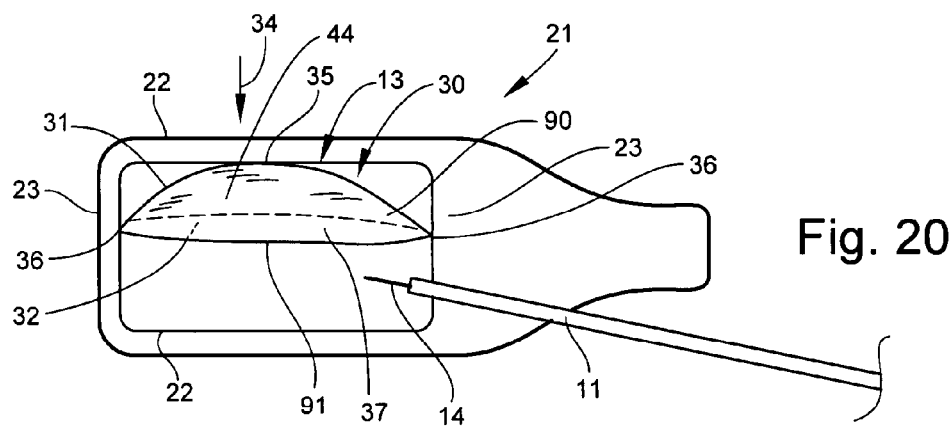
FIG. 20 is a cross-sectional view of a vertebral body showing the bone support device in FIG. 18, in a fully deployed configuration in contact with an endplate and walls of the vertebral body in an embodiment of the present invention.

FIGS. 18-20 illustrate another embodiment of the bone support and/or barrier device 13 configured to guide and or control the distribution of bone filler material injected into the interior of a bone. In this embodiment, the bone support and/or barrier device 13 can comprise a disc 90 of material that can be deployed into the interior of a bone. "Disc" refers to the deployed configuration of the device 13, which can be, for example, an oval 65, circular, semi-circular 68, dome 66, tubular, or U-shaped configuration. The disc 90 can have an outer surface 31 and an inner surface 32.

In some embodiments, the bone support and/or barrier device disc 90 can comprise a barrier material 37 adapted to restrict flow of bone filler material from the inner surface 32 to the outer surface 31 of the disc 90 without providing any additional structural support to a bony structure. That is, the barrier material 37 comprising the disc 90 can be a flexible, non-rigid material. For example, the bone support and/or barrier device disc 90 comprising pliable, non-rigid material can be deployed adjacent a compromised area within a vertebral body 21, such as a fractured endplate 22, before filling a void in the vertebral body 21 with bone cement. In this manner, the bone barrier device disc 90 can help support the integrity of such a compromised bony structure by helping prevent leakage of bone cement from the vertebral body 21.

In some embodiments, the bone barrier device 13 may be deployed such that the disc 90 contacts no portion of bone. For example, when the bone barrier device 13 is deployed inside the vertebral body 21, the disc 90 may be positioned such that the disc 90 material is free from contact with the endplates 22 and/or the vertebral body walls 23.

In other embodiments, the bone barrier device 13 may be deployed such that the disc 90 can contact the first portion of bone 35 and/or the second portion of bone 36. For example, the bone barrier device 13 may be deployed into a position such that a portion of the outer surface 31 of the disc 90 may contact the vertebral body endplate 22 (that is, the first bone portion 35). The perimeter 91 of the bone barrier device disc 90 can extend away from the endplate 22. In an embodiment, the perimeter of the disc 90 can contact the cortical bone 24 of the vertebral body walls 23 (that is, the second bone portion 36), which may help maintain the device 13 in a desired position.

In an alternative embodiment, the disc 90 can comprise a sufficient rigidity such that the axial load 34 placed on the first portion of the bone (endplate 22) can be transferred through the bone support device disc 90 to the second portion of the bone (vertebral body walls 23), thereby providing support to the first bone portion (endplate 22).

Embodiments of the bone barrier device disc 90 can have various deployed configurations. For example, the deployed disc 90 configuration can be oval 65, circular, semi-circular 68, dome 66, tubular, or U-shaped configuration. In an embodiment in which the bone support and/or barrier device disc 90 comprises a tubular shape, the disc 90 can be oriented such that opposing sides of the tubular disc 90 can contact the superior and inferior endplates 22 in the vertebral body 21.

Such a bone support and/or barrier device disc 90 having oppositely oriented sides may be desirable for use in a vertebral body 21 in which both superior and inferior endplates 22 are compromised.

Some embodiments of the bone support and/or barrier device 13 may be permanently implanted in the interior of a bone. In embodiments in which the bone support and/or barrier device disc 90 can be left permanently in place, the device 13 can be made from biocompatible materials such as stainless steel, a flexible metal alloy such as Teflon®, and/or shape memory materials such as Nitinol. In other embodiments, the bone support and/or barrier device disc 90 may be made from bioresorbable materials, such as bioresorbable polymers, such that the device 13 can eventually resorb into the surrounding tissue.

The disc 90 material can comprise a barrier material 37 adapted to prohibit substantially all flow of bone filler material from the inner surface 32 of the disc 90 of the deployed device to the outer surface 31 of the disc 90. In this manner, the device 13 can help guide and or control the distribution of bone filler material as it is injected into a void in the bone and prevent leakage of the bone filler material through a compromised bony structure adjacent the disc 90. In an embodiment, the barrier material 37 can comprise an open weave pattern adapted to reduce, but not necessarily stop, the flow of bone filler material from the inner surface 32 to the outer surface 31 of the device 13. For example, the barrier material 37 may comprise an open weave, mesh, and/or through hole configuration in which the open area is sufficiently fine to contain most of the flowable bone cement injected adjacent the inner surface 32 of the disc 90 to prevent leakage outside the vertebral body 21 and still allow enough bone cement to penetrate the barrier material 37 so as to form a bond with the surface of the cortical bone 24 adjacent the outer surface 31 of the disc 90. In some embodiments, the barrier material 37 can have a porosity sufficient to allow nutrients to diffuse through the barrier material 37. The barrier material 37 can comprise Teflon®, Dacron®, or similar biocompatible material.

Some embodiments of the bone support device and/or barrier disc 90 can be inserted into an interior body region such as a vertebral body 21 via a minimally invasive technique. For example, the delivery cannula 11 having a hollow lumen can be percutaneously inserted to the interior of a vertebral body 21. The bone support and/or barrier device disc 90 can be releasably attached in an undeployed configuration to the distal end 16 of the elongate member 14. The elongate member 14 and the attached bone support and/or barrier device disc 90 can be inserted through the lumen of the delivery cannula 11 into the vertebral body 21. When the bone support and/or barrier device disc 90 is in a desired position in the vertebral body 21, the disc 90 can be deployed into a deployed configuration, for example, into no contact with bone, or into contact with the endplate 22, vertebral body walls 23, and/or other bony structures in the vertebral body 21. Then, the bone support and/or barrier device disc 90 can be released from the elongate member 14, and the elongate member 14 and delivery cannula 11 removed from the vertebral body 21. With the bone support and/or barrier device disc 90 in a desired position, for example, adjacent the target endplate 22, a bone filler material can be injected into the void in the vertebral body 21 adjacent the inner surface 32 of the disc 90. The bone support and/or barrier device disc 90 can thus provide a barrier to restrict flow of the bone filler material through a compromised endplate 22 and into undesired areas.

An embodiment of the bone support and/or barrier device disc 90 can have an undeployed configuration that can be wrapped about the elongate member 14, as shown in FIG. 18. Expansion of the expandable body 17 inside the wrapped disc 90 can cause the disc 90 to unwrap to its deployed configuration, as shown in FIGS. 19 and 20.

In some embodiments, the bone support and/or barrier device disc 90 can be adapted so that the outer surface 31 of the disc 90 can be selectively oriented toward a desired portion of a bone. In certain embodiments, the expandable body 17 can be used to orient the disc 90 into various positions within the bone. For example, the bone support and/or barrier device disc 90 can be partially expanded with the expandable device 17 and rotated, or otherwise oriented, such that the outer surface 31 of the disc 90 is adjacent a compromised endplate 22 or vertebral body wall 23. The expandable device 17 can then be further expanded to fully deploy the bone support and/or barrier device disc 90. With the disc 90 in place, the expandable body 17 can be deflated and removed. In other embodiments, the bone support and/or barrier device disc 90 can be oriented to a desired position relative to areas within a bony structure in which it has been delivered in other manners and using other apparatus. Once the disc 90 is fully deployed and positioned, the disc 90 can be released from the elongate member 14. The void can then be filled with a flowable bone filler material through the delivery cannula 11. In this way, a user can selectively guide and or control distribution of bone filler material within a bony structure and/or helping prevent leakage of bone filler material from a weakened or compromised area.

In certain embodiments, the bone barrier device disc 90 can be sized so as to span across substantially all of a vertebral body endplate 22 when in its deployed configuration. Alternatively, the bone barrier device disc 90 can be sized to span less than substantially all of the endplate 22 when fully deployed. In some embodiments, a plurality of the bone barrier device discs 90 can be used together to guide and or control distribution of bone filler material within a bony structure.

During the process of expanding the expandable body 17 against a compromised bony structure, for example, in a vertebral body compression fracture reduction procedure, the expandable body 17 may exert enough pressure on the bony structure, such as the endplate 22, to initiate a fracture or to extend an existing fracture. An embodiment of the bone support and/or barrier device 13 can be expanded with the expandable body 17 against a compromised endplate 22. In this manner, the bone barrier device disc 90 can provide a mechanism by which the distribution of bone filler material injected into the bony structure can be guided and/or controlled. As a result, leakage of the bone cement through the compromised endplate 22 can avoided.

The present invention may provide a system useful for supporting a bony structure in a human or animal. An embodiment of such a system 10 can comprise the delivery cannula 11 having a hollow lumen that can be percutaneously inserted into an interior of a bone, and an elongate member 14 insertable through the lumen of the delivery cannula 11. An implantable bone support and/or barrier device 13 comprising an outer surface 31 and an inner surface 32 can be releasably attached to the distal end 16 of the elongate member 14 in an undeployed configuration. Some embodiments of the system 10 can further comprise a deployment mechanism that can be inserted through the lumen of the delivery cannula 11 and actuated to deploy the bone support and/or barrier device 13 into a deployed configuration in the interior of the bone. Some embodiments of the system 10 can further comprise a release mechanism adapted to release the bone support and/or barrier device 13 from the elongate member 14.

In such an embodiment of a system 10, in the deployed configuration, at least a first portion of the bone support and/or barrier device 13 can contact a first portion of the bone, such as a vertebral body endplate 22. A second portion of the bone support and/or barrier device 13 can contact a second portion of the bone, such as vertebral body walls 23. In this manner, the axial load 34 placed on the first bone portion can be transferred through the device 13 to the second bone portion, thereby supporting the first bone portion.

In some embodiments of a bone support system 10, the deployment mechanism can comprise the expandable body 17 adapted to be disposed inside the bone support and/or barrier device 13 and to expand the device 13 into the deployed configuration. In certain embodiments, the deployment mechanism can include a sheath (not shown) covering the device 13 in the undeployed configuration such that the sheath can be removed to uncover the device 13 for deployment into the deployed configuration.

In some embodiments of a system 10, the bone support and/or barrier device 13 can have a barrier material 37 attached to the device 13. The barrier material 37 can be adapted to prohibit substantially all flow of bone filler material from the inner surface 32 to the outer surface 31 of the device 13. In this manner, the device 13 can help prevent leakage of bone filler material through a compromised bony structure adjacent the barrier material 37. Alternatively, the barrier material 37 can comprise an open weave, mesh, and/or through hole pattern adapted to reduce, but not necessarily stop, the flow of bone filler material from the inner surface 32 to the outer surface 31 of the device 13. In some embodiments, the barrier material 37 can have a porosity sufficient to allow nutrients to diffuse through the barrier material 37.

Some embodiments of the bone support system 10 can include a radiopaque marking pattern in communication with components of the system 10. For example, a radiopaque marking pattern can be in communication with the delivery cannula 11, the elongate member 14, the bone support and/or barrier device 13, and/or other components of the system 10. Components having a radiopaque marking pattern can be monitored fluoroscopically during and after placement into an interior body region so as to guide the component(s) into desired position(s).

Some embodiments of the bone support system 10 can include a plurality of the bone support and/or barrier devices 13. Each of the devices 13 can be positioned in the deployed configuration to support a separate portion of a bone.

The present invention can include embodiments of a kit useful for supporting a bony structure in a human or animal. An embodiment of such a kit can comprise the delivery cannula 11 having a hollow lumen that can be percutaneously inserted into an interior of a bone, and an elongate member 14 insertable through the lumen of the delivery cannula 11. The kit may further include an implantable bone support and/or barrier device 13 comprising an outer surface 31 and an inner surface 32 that can be releasably attached to the distal end 16 of the elongate member 14 in an undeployed configuration.

In such an embodiment of the system 10, in the deployed configuration, at least a first portion of the bone support and/or barrier device 13 can contact a first portion of the bone, such as a vertebral body endplate 22. A second portion of the bone support and/or barrier device 13 can contact a second portion of the bone, such as vertebral body walls 23. In this manner, the load 34 placed on the first bone portion can be transferred through the device 13 to the second bone portion, thereby supporting the first bone portion.

Some embodiments of the kit can further comprise a deployment mechanism that can be inserted through the lumen of the delivery cannula 11 and actuated to deploy the bone support and/or barrier device 13 into a deployed configuration in the interior of the bone. In some embodiments, the deployment mechanism can comprise the expandable body 17 adapted to be disposed inside the bone support device 13 and to expand the device 13 into the deployed configuration. In certain embodiments, the deployment mechanism can include a sheath (not shown) covering the device 13 in the undeployed configuration such that the sheath can be removed to uncover the device 13 for deployment into the deployed configuration. Some embodiments of a kit can further comprise a release mechanism adapted to release the bone support and/or barrier device 13 from the elongate member 14.

In some embodiments of a kit, the bone support and/or barrier device 13 can have a barrier material 37 attached to the device 13. In other embodiments, the bone support and/or barrier device 13 can comprise the barrier material 37 without any other structural support elements. The barrier material 37 can be adapted to prohibit substantially all flow of bone filler material from the inner surface 32 to the outer surface 31 of the device 13. In this manner, the device 13 can help prevent leakage of bone filler material through a compromised bony structure adjacent the barrier material 37. Alternatively, the barrier material 37 can comprise an open weave, mesh, and/or through hole pattern adapted to reduce, but not necessarily stop, the flow of bone filler material from the inner surface 32 to the outer surface 31 of the device 13. In some embodiments, the barrier material 37 can have a porosity sufficient to allow nutrients to diffuse through the barrier material 37.

Some embodiments of a kit can include a radiopaque marking pattern in communication with components of the kit. For example, a radiopaque marking pattern can be in communication with the delivery cannula 11, the elongate member 14, the bone support and/or barrier device 13, and/or other components of the kit. Components having a radiopaque marking pattern can be monitored fluoroscopically during and after placement into an interior body region so as to guide the component(s) into desired position(s).

Some embodiments of a bone support kit can include a plurality of the bone support and/or barrier devices 13. Each of the devices 13 can be positioned in the deployed configuration to support a separate portion of a bone.

In some embodiments, a kit can comprise various combinations of these and/or other components. For example, the kit may further include additional surgical instruments.

Figure 21:
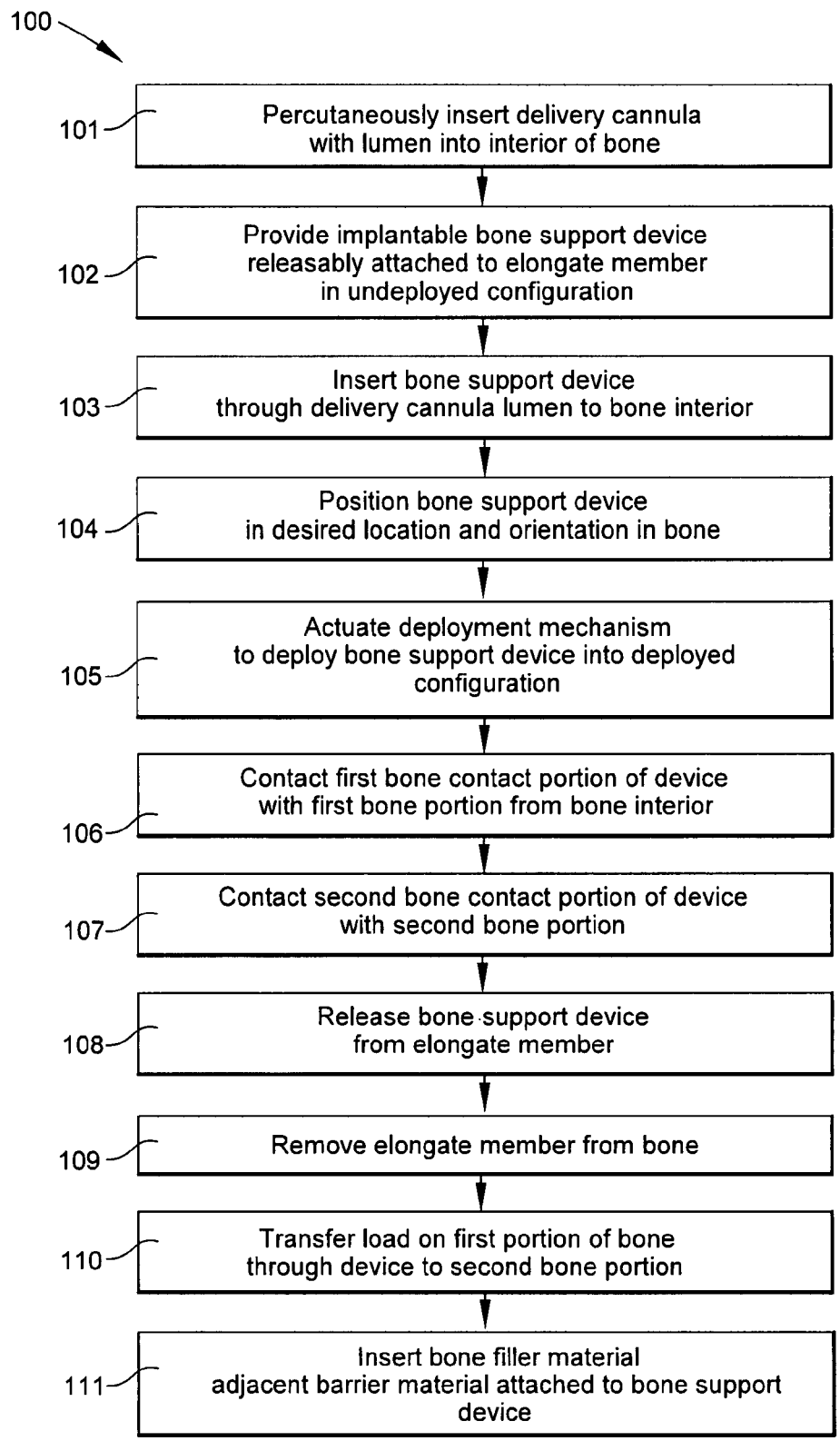
FIG. 21 is a flow chart illustrating a method for supporting a bone in an embodiment of the present invention.

The present invention can include embodiments of methods for supporting a bone or bony structure in a human or animal. One embodiment of a such a method 100, as illustrated in FIG. 21, can include percutaneously inserting (101) the delivery cannula 11 having a hollow lumen into the interior of a bone. An embodiment of the method 100 can include providing (102) an implantable bone support and/or barrier device 13 comprising an outer surface 31 and an inner surface 32. The bone support device 13 can be releasably attached to the distal end 16 of the elongate member 14 in an undeployed configuration. The elongate member 14 and attached bone support and/or barrier device 13 can be inserted (103) through the lumen of the delivery cannula 11 into the interior of the bone.

Once inside the bone, the bone support and/or barrier device 13 can be positioned (104) in a desired location and/or orientation in the bone. A deployment mechanism can be actuated (105) to deploy the bone support and/or barrier device 13 into a deployed configuration. In some embodiment, in the deployed configuration, a first portion of the device can contact (106) at least a first portion of the bone from the interior of the bone, and a second portion of the device can contact (107) at least a second portion of the bone. In this manner, the load 34 placed on the first portion of the bone can be transferred (110) through the device 13 to the second portion of the bone, thereby providing support to the first bone portion. The bone support and/or barrier device 13 can be released (108) from the elongate member 14, and the elongate member 14 can be removed (109) from the bone. In some embodiments, a bone filler material can be inserted (111) adjacent the device 13 to provide support to the bone.

In other embodiments of the method 100, the bone support and/or barrier device 13 may be percutaneously delivered to a target surgical site using a variety of techniques. For example, a small insertion cannula (not shown) having a sharp tip, for example, a trocar cannula, can be used to penetrate tissue to the surgical site. A guide wire (not shown) may be inserted through the insertion cannula. The insertion cannula can be removed, leaving the guide wire in place. The elongate member 14 and attached bone support and/or barrier device 13 can then be guided over the guide wire to the surgical site. When the bone support and/or barrier device 13 is in a desired position, the guide wire can be removed from the elongate member 14.

In some embodiments of the method 100, a plurality of the bone support and/or barrier devices 13 can be provided. Each of the plurality of the devices 13 can be deployed in a bone to support a separate portion of the bone.

In some embodiments of the method 100, the deployment mechanism can comprise the expandable body 17. The expandable body 17, for example, a balloon bone tamp, can be expanded to, for example, move endplates 22 so as restore height to the vertebral body 21. The deployment mechanism can be actuated so as to expand the expandable body 17 inside the bone support and/or barrier device 13 to expand the device 13 into its deployed configuration. In some embodiments, the deployment mechanism can further include a sheath covering the device 13 in the undeployed configuration. The sheath can be removed to uncover the device 13 for deployment into its deployed configuration.

In some embodiments of the method 100, the bone support and/or barrier device 13 can include a barrier material 37 attached to the device 13. The barrier material 37 can be adapted to prohibit substantially all flow of bone filler material from the inner surface 32 to the outer surface 31 of the device 13. When a bone filler material is inserted adjacent the inner surface 32 of the barrier material 37 of the bone support and/or barrier device 13, the bone filler material can be prevented from leaking outside an adjacent bony structure.

In an embodiment of the method 100, the bone support device 13 can include a central rod 40 pivotably attached about a pivot 43 to the distal end 16 of the elongate member 14, as shown in FIGS. 4-6. A plurality of support members 41 can be pivotably attached to the distal end 42 of the central rod 40 such that the support members 41 can be extended outwardly from the central rod 40. In such a method, actuating (105) the deployment mechanism can further include actuating the first mechanism 51 to pivot the central rod 40 to an approximately 90 degree angle relative to a longitudinal axis 52 of the elongate member 14. The second mechanism 53 can then be actuated to extend the support members 41 outwardly from the central rod 40 in a circular pattern. In this way, at least a portion of the outer surface 31 of the outwardly extending support members 41 can contact (106) a first portion of the bone from the bone interior, and the distal ends 45 of the outwardly extending support members 41 can contact (107) a second portion of the bone so as to provide support to the first bone portion.

The devices, systems, kits, and methods embodying the present invention can be adapted for use in many suitable interior body regions in humans and animals, wherever it may be desirable to provide support for a tissue. The illustrative embodiments are described in association with devices, systems, kits, and methods used to support bony structures. For example, the device can be utilized to provide structural support in a vertebral body of a spine or in a joint. In other embodiments, the present invention may be used in other interior body regions or types of tissue.

As used in this specification and the appended claims, the singular forms "a," "an," and "the" include plural referents unless the context clearly dictates otherwise. Thus, for example, the term "a support member" is intended to mean a single support member or a combination of support members. For the purposes of this specification and the appended claims, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by embodiments of the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of embodiments of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a stated range of "1 to 10" should be considered to include any and all sub-ranges between (and inclusive of) the minimum value of 1 and the maximum value of 10. That is, a stated range of "1 to 10" should be considered to include, for example, all sub-ranges beginning with a minimum value of 1 or more, such as 1 to 6.5, and ending with a maximum value of 10 or less, such as 5.5 to 10. Additionally, any reference referred to as being "incorporated herein" is to be understood as being incorporated in its entirety.

Although the present invention has been described with reference to particular embodiments, it should be recognized that these embodiments are merely illustrative of the principles of the present invention. Those of ordinary skill in the art will appreciate that a bone support device, system, kit, and method according to the present invention may be constructed and implemented in other ways and embodiments. In addition, where methods and steps described above indicate certain events occurring in a particular order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Accordingly, the description herein should not be read as limiting the present invention, as other embodiments also fall within the scope of the present invention.

What is claimed is:

1. A system, comprising:
a delivery cannula having a hollow lumen and percutaneously insertable into an interior of a bone;
an elongate member insertable through the lumen of the delivery cannula;
an implantable bone support device comprising a frame having an outer ring and a series of cross members' each cross member includes a first end and a second end, wherein the first end of each cross member is in contact with one point on the outer ring and the second end of each cross member is in contact with another opposite point on the outer ring such that the cross members extend continuously across the outer ring, wherein one side of the cross members is configured to form an outer surface, an opposite side of the cross members is configured to form an inner surface, the outer surface forming a dome-shaped first bone contact portion, and the outer ring forming a flat second bone contact portion, the device releasably attachable to a distal end of the elongate member in an undeployed configuration;
a deployment mechanism insertable through the lumen of the delivery cannula and actuatable to deploy the bone support device into a deployed configuration in the interior of the bone; and
a release mechanism adapted to release the bone support device from the elongate member.

2. The system of claim 1, wherein in the deployed configuration the first bone contact portion is configured to contact at least a first portion of the bone from the interior of the bone, and the second bone contact portion is configured to contact at least a second portion of the bone, and
wherein a load placed on the first portion of the bone is transferred through the device to the second portion of the bone.

3. The system of claim 2, wherein the first portion of the bone comprises an endplate of a vertebral body, and wherein the second portion of the bone comprises cortical bone around a perimeter of the vertebral body.

4. The system of claim 1, wherein the cross members form an open weave.

5. The system of claim 1, wherein the implantable bone support device comprises a shape memory material.

6. The system of claim 1, further comprising a plurality of the bone support devices, each of the devices positionable in the deployed configuration to support a separate portion of the bone.

7. The system of claim 6, wherein in the deployed configuration the first bone contact portion is configured to contact at least a first portion of the bone from the interior of the bone, and the second bone contact portion is configured to contact at least a second portion of the bone, and wherein a load placed on the first portion of the bone is transferred through the device to the second portion of the bone.

8. A system, comprising:
a delivery cannula having a hollow lumen and percutaneously insertable into an interior of a bone;
an elongate member insertable through the lumen of the delivery cannula;
an implantable bone support device comprising a frame having an outer ring and a series of cross members' each cross member includes a first end and a second end, wherein the first end of each cross member is in contact with one point on the outer ring and the second end of each cross member is in contact with another opposite point the outer ring such that the cross members extend continuously across the outer ring, wherein one side of the cross members is configured to form an outer surface, an opposite of the cross members is configured to form an inner surface, the outer surface forming a flat first bone contact portion, and
the outer ring forming a flat second bone contact portion, the device releasably attachable to a distal end of the elongate member in an undeployed configuration;
a deployment mechanism insertable through the lumen of the delivery cannula and actuatable to deploy the bone support device into a deployed configuration in the interior of the bone; and
a release mechanism adapted to release the bone support device from the elongate member.

* * * * *